United States Patent [19]
Stern et al.

[11] Patent Number: 5,863,892
[45] Date of Patent: Jan. 26, 1999

[54] USE OF PLATELET DERIVED GROWTH FACTOR IN OPHTHALMIC WOUND HEALING

[75] Inventors: Michael E. Stern, Mission Viejo; Larry A. Wheeler, Irvine; Margery A. Nicolson, Pacific Palisades, all of Calif.

[73] Assignees: Allergan Inc., Irvine; Amgen Inc., Thousand Oaks, both of Calif.

[21] Appl. No.: 257,494

[22] Filed: Jun. 9, 1994

Related U.S. Application Data

[63] Continuation of Ser. No. 842,306, Feb. 26, 1992, abandoned.
[51] Int. Cl.$^6$ .................................................. A61K 38/18
[52] U.S. Cl. ............................ 514/12; 514/21; 530/399
[58] Field of Search ........................ 514/12, 21; 530/399

[56] References Cited

U.S. PATENT DOCUMENTS

| | | | |
|---|---|---|---|
| 4,939,135 | 7/1990 | Robertson et. al. | 514/179 |
| 4,983,580 | 1/1991 | Gibson | 514/21 |
| 5,013,714 | 5/1991 | Lindstrom et al. | 214/21 |
| 5,034,375 | 7/1991 | Antoniades et. al. | 514/12 |

FOREIGN PATENT DOCUMENTS

| | | |
|---|---|---|
| 339905 | 11/1989 | European Pat. Off. . |
| 900741 | 7/1991 | WIPO . |
| 91-08761 | 7/1991 | WIPO . |

OTHER PUBLICATIONS

Gartry et al., "Excimer Laser Photorefractive Keratectomy," Ophthalmology vol. 99, No. 8, 1992, p. 1212.

Van Mellaert et al., "On the Safety of 193–Nanometer Excimer Laser Refractive Corneal Surgery," Refractive & Corneal Surgery vol. 8, 1992, pp. 235–238.

Lohmann et al., "Plasmin–and Plasminogen–Activator Inhibitors After Excimer Laser Photorefractive Keratectomy: New Concept in Prevention of Postoperative Myopic Regression and Haze,"Refractive & Corneal Surgery, vol. 9, 1993, pp. 301–302.

Arshinoff, et al., "The Use of Topical Nonsteroidal Anti–inflammatory Drugs in Excimer Laser Photorefractive Keratectomy," Third American Intnl. Congress on Cataract, IOL and Refractive Surgery, 1993, pp. 1–21.

Nakada et al., "Effect of pdgf, igf and egf on corneal epithelial wound healing and reinnervation," Investigative Ophthalmology and Visual Science (4 Abstract Issue) vol. 31, 1990, St. Louis, p. 54.

Hersh et al., "Effect of Platelet–Derived Growth Factor on Cultures Keratocytes and Its Uptake by the Cornea," Investigative Opthalmology and Visual Science vol. 29, 1988, St. Louis, p. 313.

Hoppenreijs et al., "Effects of Platelet–Derived Growth Factor (PDGF) on Wounded Human Corneal Endothelium in Organ Culture,"X Intnl. Congress of Eye Research, vol. 55, No. S1, 1992, p. S99.

Stern, et al., "A Multilevel Approach to the Evaluation of Platelet Derived Growth Factor (PDGF) on Rabbit Corneal Wound Healing.," X Intnl. Congress of Eye Research, vol. 55, No. S1, 1992, p. S98.

Banks, Allen R., "The Role of Growth Factors in Tissue Repair II, Epidermal Growth Factor", Chapter 10, Molecular and Cellular Biology of Wound Repair, 1986, pp. 253–263.

Fox, Gary M., "The Role of Growth Factors in Tissue Repair III, Fibroblast Growth Factor", Chapter 11, Molecular and Cellular Biology of Wound Repair, 1986, pp. 265–271.

Adelmann–Grill, B, et al. "Chemotactic migration of normal dermal fibroblasts toward epidermal growth factor and its modular by platelet–derived growth factor and transforming growth factor–beta, "Eur. J. Cell. Biol., 51–322–326, 1990.

Cromack, Douglas T., et al., "Current Concepts in Wound Healing: Growth Factor and Macrophage Interaction," Journal of Trauma, 30:S129–133, 1990.

Antoniades, Harry N., et.al., "Injury induces in vivo expression of platelet–derived growth factor (PDGF) and PDGF receptor mRNAs in sknin epithelial cells and PDGF mRNA in connective tissue fibroblasts, " Proc. National. Acad. Sci USA, 88:565–569 1991.

Ross, R., et. al., "Platelet–derived growth factor and its role in health and disease," Philos. Trans. R. Soc. Lond. Biol. 327:327:155–169, 1990.

Sun et al., Nature, vol. 269, (5628), pp. 489–493, Oct. 1977, Medline: 78010468.

Bennett et al., Am. J. Surg., vol. 166, pp. 74–81, 1993.

Kunkle et al., Invest. Ophthalmol., Visual Sci., vol. 32(4), p. 1159, 1991.

*Primary Examiner*—Chhaya D. Sayala
*Attorney, Agent, or Firm*—Knobbe Martens Olson, & Bear, LLP

[57] ABSTRACT

A method of accelerating corneal wound healing in the corneal anterior stroma and/or improving the quality of wound healing in a mammal comprises: (1) providing an ophthalmically compatible solution of platelet-derived growth factor; and (2) applying the solution to the cornea of a mammal at the time of or subsequent to occurrence of a corneal wound in a quantity sufficient to accelerate clinically detectable healing, the healing being accelerated through proliferation of epithelial cells and/or keratocytes of the cornea stimulated by application of the platelet-derived growth factor to the cornea. The platelet-derived growth factor can be selected from the group consisting of the AA isoform, the AB isoform, the BB isoform, and mixtures thereof. A preferable form of platelet-derived growth factor is a recombinantly-derived refolded B-chain homodimer of 119 amino acids, having the amino acid sequence of SEQ ID NO: 1. The concentration of platelet-derived growth factor in the solution can be from about 10 $\mu$g/ml to about 1000 $\mu$g/ml, preferably from about 50 $\mu$g/ml to about 500 $\mu$g/ml, and most preferably about 100 $\mu$g/ml.

15 Claims, 15 Drawing Sheets

```
     1 CTAGAAGGAGGAATAACATATGTCTCTGGGTTCGTTAACCATTGCGGAACCGGCTATGAT
       ---------+---------+---------+---------+---------+---------+
       TTCCTCCTTATTGTATACAGAGACCCAAGCAATTGGTAACGCCTTGGCCGATACTA
                           MetSerLeuGlySerLeuThrIleAlaGluProAlaMetIl
                           1

61 TGCCGAGTGCAAGACACGAACCGAGTGTTCGAGATCTCCCGGCCCTCATCGACCGCAC
       ---------+---------+---------+---------+---------+---------+
       ACGGCTCACGTTCTGTGCTTGGCTCCACAAGCTCTAGAGGGCCGGGAGTAGCTGGCGTG
       eAlaGluCysLysThrArgThrGluValPheGluIleSerArgArgLeuIleAspArgTh
       14

121 CAATGCCAACTTCCTGGTGTGGCCGCCCTGCGTGGAGGTGCAGGCGTGCTCCGGCTGTTG
       ---------+---------+---------+---------+---------+---------+
       GTTACGGTTGAAGGACCACACCGGCGGGACGCACCTCCAGGTCGCGACGAGGCCGACAAC
       rAsnAlaAsnPheLeuValTrpProProCysValGluValGlnArgCysSerGlyCysCy
       34
```

USE OF PLATELET DERIVED GROWTH FACTOR IN OPHTHALMIC WOUND HEALING

This is a continuation of application Ser. No. 07/842,306 filed on Feb. 26, 1992, now abandoned.

BACKGROUND OF THE INVENTION

The invention relates to the use of platelet-derived growth factor (PDGF) to stimulate ophthalmic wound healing, particularly wounds to the cornea.

Corneal wounds frequently arise from trauma to the eye, such as may occur in automobile accidents, industrial accidents, and wounds caused by weapons. Wounds to the eye also occur as the unavoidable consequence of surgery, such as cataract surgery, penetrating keratoplasty, glaucoma filtering surgery, retinal surgery such as retinal reattachment, and refractive surgery such as laser corneal ablation or radial keratotomy. Non-healing corneal ulcers may also arise from pathological non-traumatic causes, such as diabetes.

The healing of these wounds can frequently be slow and difficult, complicating recovery from trauma or the postoperative course of surgery. There is, therefore, a need for a readily applicable method of accelerating ophthalmic wound healing, particularly of corneal wounds.

Additionally, the quality of healing of corneal wounds is frequently poor, leading to scarring and other vision-impairing consequences. Therefore, there also is a need for a method that can improve the quality of healing of corneal wounds.

Recently, much attention has been paid to the use of growth factors to accelerate wound healing, particularly of skin. Growth factors are agents which cause cells to migrate, differentiate, transform, or mature and divide. These factors are polypeptides which can usually be isolated from many different normal and malignant mammalian cell types. Some growth factors can be produced by genetically-engineered microorganisms such as bacteria (*Escherichia coli*) and yeasts. See, for example, Chapters 10 and 11 of *Molecular and Cellular Biology of Wound Repair* (1986), incorporated herein by reference. Among these growth factors are included epidermal growth factor (EGF), transforming growth factors alpha and beta (TGFα, TGFβ$_1$, and TGFβ$_2$), fibroblast growth factor (FGF), insulin-like growth factor (IGF), nerve growth factor (NGF), and platelet-derived growth factor (PDGF). These are described in U.S. Pat. No. 4,939,135 to Robertson et al., incorporated herein by this reference.

The use of PDGF to accelerate wound healing in skin and connective tissue has been studied (Antoniades et al., *Proc. Natl. Acad. Sci. USA* 88:565–569 (1991); Cromack et al., *J. Trauma* 30:S129–133 (1990); Ross et al., *Philos. Trans. R. Soc. Lond. (Biol.)* 327:155–169 (1990)). However, conditions in the cornea are substantially different than those in skin and connective tissue. For example, the corneal epithelium is continually washed with tear fluid which contains a significant quantity of EGF. It is believed that the presence of one growth factor may compete for or interfere with the response to other growth factors (Adelman-Grill et al., *Eur. J. Cell. Biol.* 51:322–326 (1990)). Thus, there is a need for a growth factor that will work in corneal tissue as opposed to skin or connective tissue, and that can work to promote corneal wound healing even in the presence of other growth factors.

Additionally, re-innervation of the cornea is highly desirable but frequently is delayed during healing. Failure of re-innervation can lead to loss of function, such as the failure of maintenance of the corneal epithelium. It is therefore desirable that a treatment that accelerates corneal wound healing also accelerates re-innervation.

SUMMARY

A method of accelerating and/or improving the quality of corneal wound healing in a mammal by the application of PDGF meets these needs. The method comprises:

(1) providing an ophthalmically compatible solution of platelet-derived growth factor; and (2) applying the solution to the cornea of a mammal at the time of or subsequent to occurrence of a corneal wound in a quantity sufficient to accelerate clinically detectable healing, the healing being accelerated through proliferation of epithelial cells and/or keratocytes of the cornea stimulated by application of the platelet-derived growth factor to the cornea.

The platelet-derived growth factor can be selected from the group consisting of the AA isoform, the AB isoform, the BB isoform, and mixtures thereof. Preferably, the platelet-derived growth factor is the BB isoform.

In one preferred version, the platelet-derived growth factor is a recombinantly-derived refolded B-chain homodimer of 119 amino acids, having the amino acid sequence of S-L-G-S-L-T-I-A-E-P-A-M-I-A-E-C-K-T-R-T-E-V-F-E-I-S-R-R-L-I-D-R-T-N-A-N-F-L-V-W-P-P-C-V-E-V-Q-R-C-S-G-C-C-N-N-R-N-V-Q-C-R-P-T-Q-V-Q-L-R-P-V-Q-V-R-K-I-E-I-V-R-K-K-P-I-F-K-K-A-T-V-T-L-E-D-H-L-A-C-K-C-E-T-V-A-A-A-R-P-V-T-R-S-P-G-G-S-Q-E-Q-R (SEQ ID NO: 1).

The concentration of platelet-derived growth factor in the solution can be from about 10 μg/ml to about 1000 μg/ml. Preferably, the concentration is from about 50 μg/ml to about 500 μg/ml. Most preferably, the concentration is about 100 μg/ml.

The solution can be applied at least once or more to the cornea subsequent to occurrence of the corneal wound. Preferably, the solution is applied from once to three times, e.g., at about 2 hours, at about 8 hours, and at about 24 hours after occurrence of the wound. Alternatively, the solution can be applied to once or more to the cornea at the time of occurrence of the corneal wound.

The wound can result from the effects of a surgical laser or be a consequence of diabetes.

Clinically detectable healing includes improvement in the quality of corneal wound healing. The improvement in the quality of corneal wound healing can comprise a clinically detectable decrease in abnormal epithelial sloughing in recurrent corneal ulcers or a clinically detectable decrease in scar formation, or both.

Application of PDGF can also accelerate clinically detectable re-innervation of the corneal epithelium after occurrence of a corneal wound that denervates at least a portion of the corneal epithelium. The PDGF is applied in a quantity sufficient to accelerate clinically detectable re-innervation of the corneal epithelium. This represents one of the unexpected results of PDGF treatment.

Another aspect of the present invention is a pharmaceutical composition for application to the cornea of a mammal for accelerating and/or improving the quality of corneal wound healing comprising:

(1) water;

(2) an ophthalmically compatible solution of platelet-derived growth factor comprising at least about 10 μg/ml of platelet-derived growth factor; and (3) buffer to adjust the pH to within a range of from about 5 to about 8.

The composition can be in dosage unit form.

Yet another aspect of the present invention is a tablet for preparation of a pharmaceutical composition for application to the cornea of a mammal for accelerating and/or improving the quality of corneal wound healing comprising:

(1) a quantity of platelet-derived growth factor sufficient to accelerate and/or improve the quality of wound healing; and (2) non-toxic ophthalmically-acceptable excipients which are suitable for the manufacture of tablets.

BRIEF DESCRIPTION OF THE DRAWINGS

These and other features, aspects, and advantages of the present invention will become better understood with reference to the following description, appended claims, and accompanying drawings where:

FIG. 14A–14B are a diagram of the DNA sequence (SEQ ID NO: 6) used to express rPDGF $B_{119}$ in the *Escherichia coli* expression vector pCFM1156, as set forth in Example 1, and the resulting protein sequence (SEQ ID NO: 1) of rPDGF $B_{119}$.

DESCRIPTION

Figure 1:
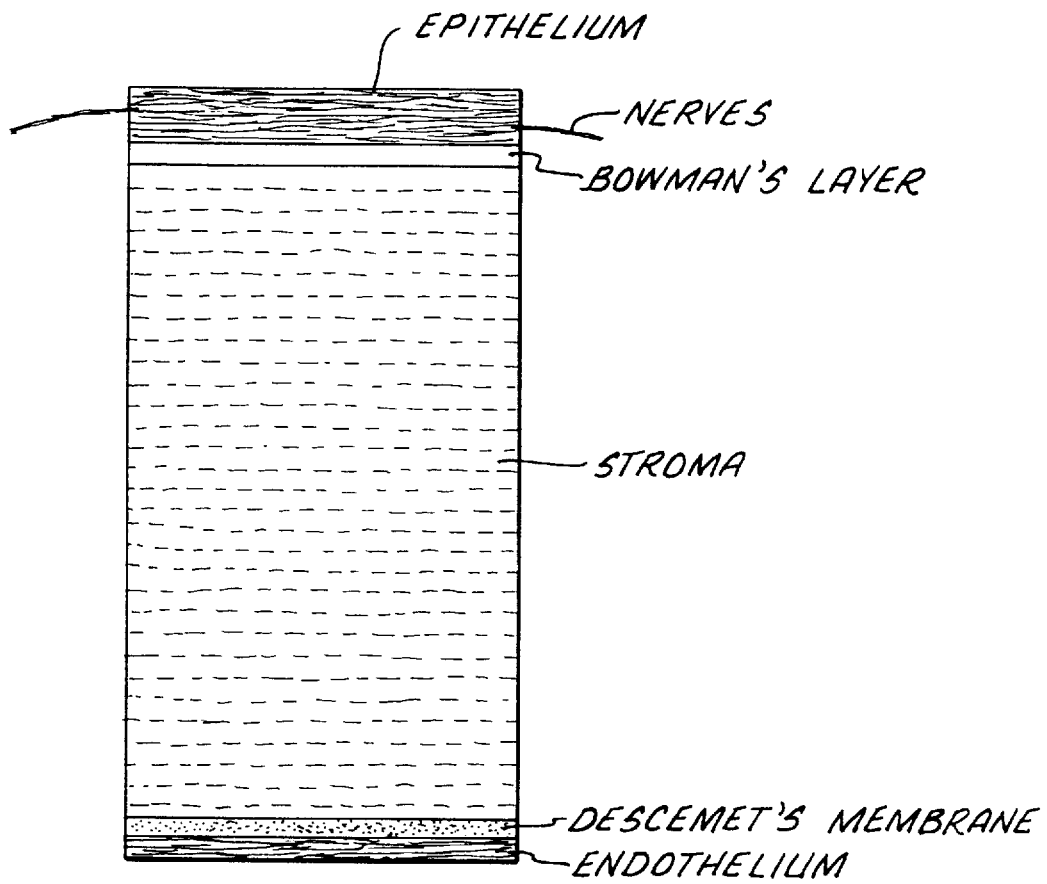
FIG. 1 is a diagrammatic depiction of the mammalian cornea, showing the layers making up the cornea and the innervation of the epithelium.

We have discovered that platelet-derived growth factor (PDGF), when applied to wounds in the mammalian cornea, can substantially accelerate healing of the wounds.

Natural human PDGF is comprised of two polypeptide chains forming a dimer. The two chains are the A chain, composed of 124 amino acids, and the B chain, composed of 160 amino acids. Each chain has a cysteine residue; the chains are joined through disulfide bonding. The separate chains have been identified and sequenced (Waterfield et al., *Nature* 304:35–39 (1983); Doolittle et al., *Science* 221:275–277 (1983); Betsholtz et al., *Nature* 320:695–699 (1986); Weich et al., *FEBS Lett.* 198:344–348 (1986); Hoppe et al., *FEBS Lett.* 223:234–246 (1987)). The active growth factor can be assembled as any combination of the two chains, the AA or the BB homodimers or the AB heterodimer. These different combinations are referred to as isoforms.

The different isoforms bind to different classes of PDGF receptor (Bowen-Pope et al., *J. Biol. Chem.* 264:2502–2508, (1989)) and exert different effects on the cells on which they act (Sachinidis et al., *J. Biol. Chem.* 265:10238–10243 (1990)). Each of the receptors binds one and only one subunit, so one dimeric PDGF molecule can bind two receptor molecules (Sachinidis et al., supra).

The basic method of accelerating wound healing comprises: (1) providing an ophthalmically compatible solution of platelet-derived growth factor (PDGF); and (2) applying the solution to the cornea of a mammal at the time of or subsequent to occurrence of a corneal wound in a quantity sufficient to accelerate clinically detectable healing, the healing being accelerated through proliferation of epithelial cells and/or keratocytes of the cornea stimulated by application of the platelet-derived growth factor to the cornea.

The application of PDGF to the cornea can also improve the quality of wound healing. Due to the fact that PDGF induces epithelial secretion of basement membrane components, the quality of healing would be improved as measured by a decrease in abnormal epithelial sloughing in recurrent corneal ulcers after healing. In addition, corneal histology after incision shows an increase in the rate of collagen repair as indicated by the presence of large numbers of activated keratocytes around the incision, which could result in a decrease in resulting scar formation. The term "quality of wound healing" is therefore defined herein as either a clinically detectable decrease in abnormal epithelial sloughing in recurrent corneal ulcers, a clinically detectable decrease in scar formation, or both.

Of particular importance is the fact that the application of PDGF can also accelerate re-innervation of the corneal epithelium, which is crucial to preserving the structural integrity and function of the cornea. The return of corneal innervation and sensation to the ocular surface after a wound is important to the maintenance of the corneal epithelium. Re-innervation of an area of the ocular surface after an epithelial wound is thought to be linked sequentially to the repair of the epithelial defect. Therefore, corneal innervation would be restored faster to the cornea in which the epithelium healed faster.

A diagram of the cornea is shown in FIG. 1, including the nerves innervating the corneal epithelium. If these nerves are severed as occurs whenever the epithelium is removed, the healing of the cornea can be greatly impaired.

I. THE OPHTHALMICALLY COMPATIBLE SOLUTION

A. The Platelet-Derived Growth Factor

The term "platelet-derived growth factor" (PDGF) is used herein to mean any polypeptide or complex of polypeptides having substantially the same physiological activity as any of the isoforms of natural human PDGF, regardless of the origin of the polypeptide. The PDGF can be produced by any method practiced in the art, including, but not limited to: isolation from human or animal tissue; chemical synthesis, such as solid-phase peptide synthesis; and production by bacteria, yeast, or cultured cell lines that have been genetically engineered to produce PDGF. The term PDGF also includes, but is not limited to, the following variants: (1) variants of PDGF that differ in glycosylation from naturally-occurring PDGF; (2) chemically-modified derivatives of PDGF; (3) genetically engineered molecules having PDGF activity with one or more amino-acid substitutions, additions, or deletions when their sequences are compared to natural human PDGF, including muteins in which cysteine residues are converted into other amino acid residues, and including molecules having different numbers of amino acid residues than natural human PDGF; and (4) fusion proteins in which the polypeptide responsible for PDGF is fused with another heterologous protein, such as a bacterial or yeast protein. In particular, the following recombinant molecules are included within the definition of PDGF used herein:

(1) a variant of the AA isoform in which each chain has 110 amino acid residues, the so-called "endothelial form," produced by yeast using the expression system previously used to express v-sis (Kelly et al., *EMBO J.* 4:3399–3405 (1985); Collins et al., *Nature* 328:621–624 (1987); Tong et al., *Nature* 328:619–621 (1987));

(2) a recombinantly-derived refolded B-chain homodimer of 119 amino acids, produced by *Escherichia coli* as described in Examples 1 and 2 below and in PCT Application No. WO 91/08761 by Thomason, incorporated herein in its entirety by this reference; and (3) a variant of the BB isoform in which each chain has 109 amino acid residues, produced by genetically-engineered yeast (Kelly et al., supra).

The PDGF can be of the AA isoform, the BB isoform, AB isoform, or mixtures thereof. Preferably, the PDGF is of the BB isoform.

A particularly preferred form of PDGF is a recombinantly-derived refolded B-chain homodimer of 119 amino acids having the sequence S-L-G-S-L-T-I-A-E-P-A-M-I-A-E-C-K-T-R-T-E-V-F-E-I-S-R-R-L-I-D-R-T-N-A-N-F-L-V-W-P-P-C-V-E-V-Q-R-C-S-G-C-C-N-N-R-N-V-Q-C-R-P-T-Q-V-Q-L-R-P-V-Q-V-R-K-I-E-I-V-R-K-K-P-I-F-K-K-A-T-V-T-L-E-D-H-L-A-C-K-C-E-T-V-A-A-A-R-P-V-T-R-S-P-G-G-S-Q-E-Q-R (SEQ ID NO: 1). This form of PDGF, referred to generally below as "rPDGF $B_{119}$," is produced by expression of v-sis that has undergone in vitro mutagenesis. The in vitro mutagenesis converts the amino acid residues at positions 6, 7, 101, 107, and 114 from the amino acids found in the v-sis protein to the amino acids found in the B human chain of human PDGF and inserts a stop codon at position 120. The resulting mutated gene is then inserted into an expression vector for *Escherichia coli*, pCFM1156, for expression of the rPDGF $B_{119}$. The expressed PDGF is then refolded into a dimer using glutathione as blocking agent. Further details of the preparation of rPGDF $B_{119}$ are given in Examples 1 and 2, below.

Genetic constructions to obtain the desired rPDGF $B_{119}$ can be prepared using a modification of any one of a number of methods for the recombinant production of PDGF B known to those skilled in the art. For example, one can first modify the v-sis gene to obtain the human counterpart c-sis, or use the c-sis as a starting material and then transfect the desired host cell following placement of the stop codon at any of amino acid positions 111 through 160. The stop codon is preferably placed in the c-sis or modified v-sis precursor protein coding sequence by site-directed mutagenesis of a pre-existing codon.

Alternatively, one can either synthesize the precursor protein coding sequence, or first cut back the c-sis gene or modified v-sis gene, at a appropriate restriction site near the carboxy terminus, and then rebuild the carboxy terminus of the precursor protein coding sequence to the desired end position (about 111 to about 160), using preferred codons for particular vector and host cell systems being employed. The c-sis gene or modified v-sis gene can also be cut back at an appropriate restriction site near the amino terminus, with the amino terminus being cut back to the desired starting position (preferably amino acid 1), again using preferred codons for the selected vector and host cell systems. Regardless of whether naturally occurring or synthesized starting materials, or a combination thereof, are used, a stop codon must be placed after the desired carboxy terminal amino acid of the precursor protein coding sequence; i.e., at any one of amino acid positions at about 111 to 160.

In a preferred method for obtaining the recombinant PDGF, the v-sis gene is modified to obtain the c-sis gene, after which, or concurrently therewith, a stop codon is placed at the desired location of the modified gene. The c-sis precursor protein coding sequence containing the stop codon is then inserted into a vector, which is used to transfect the desired prokaryotic host cell.

More preferably, the precursor protein coding sequence used to obtain the recombinant PDGF is an analog of the c-sis gene. The c-sis analog precursor protein coding sequence may be constructed to contain preferred codons for expression in an *E. coli* host cell. The analog of the c-sis gene may be obtained by both site-directed mutagenesis and ligation of the c-sis with synthetic carboxy and amino termini following proteolytic cleavage of the existing termini at appropriate proteolytic cleavage sites.

The v-sis gene provides an excellent starting material for obtaining a precursor protein coating sequence for obtaining recombinant PDGF. For example, in the region coding for amino acids 1–119, there are only five amino acid differences between the protein incorporated by the v-sis gene and the c-sis encoded $PDGF_{119}$ precursor protein. Two of these five amino acids in the v-sis gene can be altered by in vitro mutagenesis techniques to generate a DNA sequence coding for a protein in which the two amino acids are the same as the corresponding residues in the PDGF $B_{119}$ precursor protein. A number of methods for in vitro mutagenesis of DNA can be utilized for introducing the desired changes at codons 101 and 107. Such methods are well-known to those skilled in the art. For example, the method of Eckstein and co-workers (Taylor, et al., *Nucl. Acids Res.* 13:8764–8785 (1985); Nakamaye & Eckstein, *Nucl. Acids Res.* 14:967–969 (1986) as described in the instruction booklet for the Amersham (Arlington Heights, Ill.) "Oligonucleotide-Directed In Vitro Mutagenesis System" kit, is particularly useful in converting the isoleucine residue at amino acid 101 to a threonine residue and the alanine residue of amino acid 107 to a proline residue.

Following in vitro mutagenesis of amino acids 101 and 107, the altered v-sis DNA may then be cut back at the amino terminus with the restriction enzyme BglII, which cuts at a position corresponding to amino acid 24. The upstream portion of the gene, including the first 24 amino acids, may be restored by ligation of the downstream BglII-cut mutagenized v-sis DNA with a synthetic DNA fragment encoding; (1) an ATG translation initiation codon; (2) a serine residue at amino acid 1; and (3) the remainder of the first 24 amino acids of the c-sis encoded precursor protein. In this way, two of the other three variant amino acids, i.e., the serine residue at amino acid 6 and the valine residue of amino acid 7, are converted to the amino acids occurring in human PDGF B at these positions (threonine and isoleucine, respectively), with the upstream precursor amino acids encoded by v-sis being removed.

Cutting back from the carboxy terminus in a similar manner enables replacement of the carboxy terminus with a synthetic fragment which simultaneously alters amino acid 114 and replaces amino acid 120 with a stop codon. Preferably, mutagenized v-sis DNA is cut with the restriction enzyme SmaI, which cuts at a position corresponding to amino acid 112. A synthetic DNA fragment coding for amino acids 112–119 of the PDGF $B_{119}$ precursor protein, and a translation stop codon at position 120, may then be ligated to the SmaI-cut mutagenized v-sis DNA. The synthetic DNA also encodes a glycine residue, instead of a threonine residue, at amino acid 114 accompanying the conversion of the fifth variant amino acid to the corresponding amino acid in PDGF $B_{119}$ precursor protein.

The final DNA construct of the precursor protein coding sequence calls for amino acids 1–119 of PDGF B plus an additional methionine residue at the N terminus. This PDGF $B_{119}$ gene may be ligated into an appropriate expression vector, such as pCFM1156, and then transformed or transfected into an appropriate host cell system, preferably a prokaryote such as an E. coli host cell, with the N-terminal methionine being removed in vivo following biosynthesis in the host cell. (It is possible that some E. coli strains will fail to remove the N-terminal methionine, thereby producing a recombinant product containing an additional amino acid residue at the amino terminus.)

The preferred expression systems for the production of such recombinant PDGF B comprise procaryotic cell culture systems as discussed above, preferably E. coli.

Genetic engineering methods for the cloning and expression of recombinant PDGF analogues are disclosed in U.S. patent application Ser. Nos. 454,794, filed Dec. 19, 1989, and 624,451, filed Dec. 13, 1990, both of which are incorporated herein by this reference.

The rPDGF B analogues useful in the present invention may be isolated, refolded, and purified from the resulting host cell culture paste by any one of a number of methods known to those skilled in the art. A preferred method for refolding is described in U.S. patent application Ser. No. 451,485, which is incorporated herein by this reference.

In accordance with the preferred refolding method, a disulfide blocking agent is employed to generate a monomeric mixed disulfide intermediate, such that the free sulfhydryls of the reduced, unfolded monomeric rPDGF become blocked. This prevents the sulfhydryl groups of reduced rPDGF from prematurely forming disulfide bonds during isolation and purification. At the same time, this modification also renders the rPDGF intermediate soluble in aqueous solutions. As a consequence of this solubility, forces present in a selected aqueous environment can be used to coax the blocked monomeric intermediate into its biologically active conformation, after which unblocking may occur. Typically, unblocking results in the formation of a dimeric form of PDGF, wherein the dimeric structure is now "locked" in place by the formation of the desired intrachain and interchain disulfide bonds. This dimeric form is a homodimer.

B. Concentration

The concentration of the PDGF in the ophthalmically compatible solution can be from about 10 µg/ml to about 100 µg/ml. Preferably, the concentration is about from 50 µg/ml to about 500 µg/ml. Most preferably, the concentration of PDGF is 100 µg/ml.

C. Other Ingredients of the Solution

The ophthalmically compatible solution containing PDGF is preferably prepared in water. The solution can also contain a physiologically-acceptable surface active agent, either ionic or non-ionic, as well as conventional preservatives, anti-bacterial, or anti-fungal agents. For example, the solution can contain ethanol, glycerol, hydroxymethylcellulose, propylene glycol, polyethylene glycol, polyoxyethylenesorbitan, or vegetable oils. The conventional anti-bacterial, anti-fungal or preservative agents can include parabens, chlorobutanol, phenol, sorbic acid, thimerosal, and the like. All of these components are present in concentrations that are ophthalmically acceptable to the eye. In addition, buffers may be used to maintain the composition at physiological pH or at slightly lower pH, i.e, within a pH range of from about 5 to about 8. The buffers can be conventional buffers such as borate, citrate, phosphate, bicarbonate, or Tris-HCl. The solutions can be made isotonic by the addition of conventional osmotically active materials, such as sodium chloride and/or sugars. The solution can include other solubilizing agents including proteinaceous carriers or solubilizers, such as albumin. The solutions can further guarantee emollients such as lanolin derivatives and/or other oils for convenience and ease in application, as well as for greater tolerability. The solution can further comprise antibiotics to control infection.

Another aspect of this application is pharmaceutical compositions for application to the cornea of a mammal to accelerate and/or improve the quality of wound healing. These compositions comprise either ophthalmically compatible solutions, as described above, or tablets containing the active ingredient or ingredients, i.e., a quantity of platelet-derived growth factor sufficient to accelerate and/or improve the quality of wound healing, in a mixture with non-toxic ophthalmically-acceptable excipients which are suitable for the manufacture of tablets. The solutions can be prepared in dosage unit form. For the tablets, the excipients can be inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc, along with the PDGF and other ingredients. These tablets can be preformulated so that ophthalmically compatible solutions of PDGF suitable for application to the cornea can be prepared by dissolving the tablets in water, water mixed with ethanol, or other suitable liquids. The concentration of PDGF in the tablets is such that when the tablets are dissolved to produce the solution, the concentration of PDGF in the solution is within the concentration limits disclosed above.

II. APPLICATION OF THE PDGF SOLUTION

In performing the method of accelerating corneal wound healing in the present invention, the solution is applied to the cornea of a mammal at the time of or subsequently to occurrence of a corneal wound in a quantity sufficient to accelerate clinically detectable healing. The healing is accelerated through proliferation of epithelial cells and/or keratocytes of the cornea stimulated by application of platelet-derived growth factor to the cornea. Preferably, the application of the ophthalmically compatible solution of PDGF also acts to accelerate re-innervation of the cornea.

Typically, the solution is applied directly to the cornea at a quantity of about 10 to about 500 μl, preferably about 50 μl. The quantity of solution applied and the concentration of PDGF in the solution can readily be determined by one of ordinary skill in the art, such as by examination of the eye and photography with a slit lamp, as well as clinical observation of the patient. Multiple applications of the solution to the cornea can be made. Preferably, one or more applications are made; more preferably, from one to three applications are made. These applications can occur at about 2 hours, about 8 hours, and at about 24 hours after occurrence of the wound or the surgical procedure.

The procedure of the present invention can be employed in cases of epithelial denudement in which the basement membrane is left intact, as well as after anterior keratectomy in which the basement membrane is removed. The method of the present invention can further be used in treatment of stromal wounds such as incisions.

In particular, the procedure of the present invention can be employed to accelerate and/or improve the quality of wound healing of wounds resulting from trauma to the eye, as well as wounds resulting from surgical treatment, such as the application of surgical lasers. These treatments include cataract surgery, penetrating keratoplasty, glaucoma filtering surgery, retinal surgery such as retinal reattachment, and refractive surgery such as radial keratotomy and laser corneal ablation. The procedure of the present invention can also be used to accelerate and/or improve the quality of wound healing of lesions arising from pathological non-traumatic causes, such as the non-healing corneal ulcers of diabetes.

The presence or absence of the basement membrane and the degree of damage or wounding of the cornea may require adjustment of the dose of PDGF. This can be accomplished according to the techniques described above, and is within the skill of persons of ordinary skill in the art. Similarly, clinically detectable re-innervation of the corneal epithelium can be accelerated subsequent to occurrence of a corneal wound that denervates at least a portion of the corneal epithelium by treatment of the cornea with PDGF according to the techniques described above.

The invention is illustrated by the following examples. The examples are for illustrative purposes only and are not to be construed as limiting the scope of the invention in any manner.

EXAMPLE 1

Production of rPDGF $B_{119}$

Figure 14B:
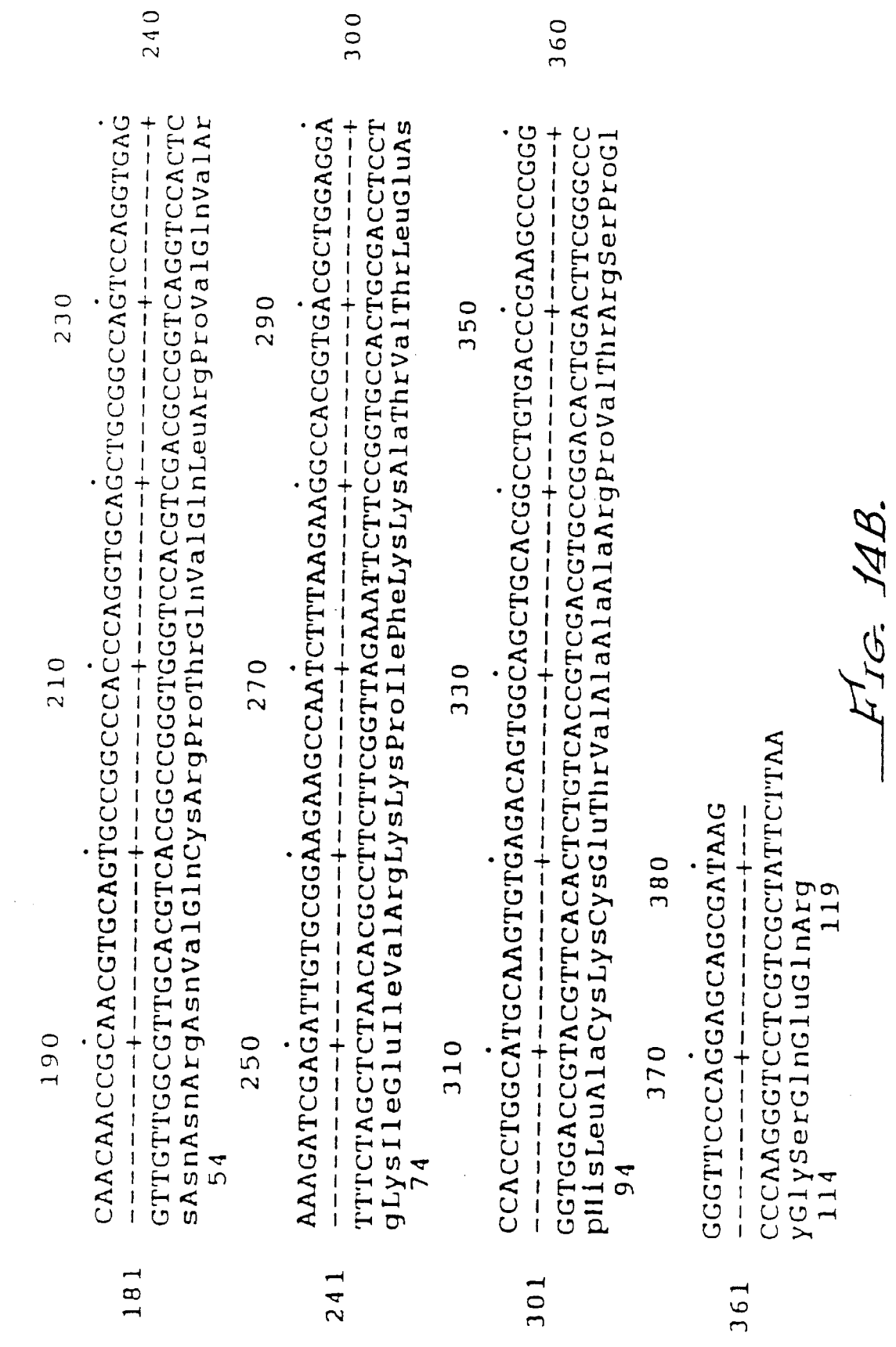

A PDGF $B_{119}$-encoding precursor protein coding sequence, shown in FIG. 14, was constructed using the v-sis gene as a starting material.
Conversion of Amino Acids 101 and 107
One μg of the plasmid pC60, a clone of the simian sarcoma virus retroviral gene (Wong-Staal et al., *Science*, 213:226–228 (1981)), was digested with restriction endonucleases SalI and XbaI, with the resulting 1183 base pair fragment then being purified by electrophoretic separation in a low-melting temperature agarose gel, in accordance with the procedure described by Maniatis et al., *Molecular Cloning—A Laboratory Manual, Cold Spring Harbor Laboratory* (1982). The purified fragment was then excised from the gel. At the same time, 0.2 μg of M13mp19 DNA was also digested with SalI and XbaI, with the large 7245 base pair band being similarly excised from a low-melting gel. Both excised gel slices were melted at 65° C., and then cooled to 37° C. All of the gel with the 7245 base pair M13mp19 fragment and one-fourth of the gel with the 1183 base pair v-sis fragment were mixed and ligated according to Struhl, *Biotechniques*, 3:452–453 (1985). The ligated DNA was transformed into *E. coli* K12 strain PG1, and a clear plaque of the M13 vector was selected and grown in liquid culture. The presence of the 1183 base pair v-sis fragment in the M13mp19 vector was confirmed by preparation of the double-stranded replicative form (RF) of the phage DNA and restriction map analysis. (Messing et al., *Nucl. Acids Res.* 9:309–321 (1981)).

The M13mp19/v-sis phage thus obtained was grown in liquid culture, and the single-stranded DNA isolated (Messing et al., supra.) This DNA was used as a template for oligonucleotide-directed in vitro mutagenesis to convert the amino acids at residues 101 and 107 to the corresponding amino acids of human PDGF B. In the first stage of this process, the ATA codon coding for isoleucine 101 was converted to ACA, coding for threonine, and the GCT codon coding for alanine 107 was converted to CCT, coding for proline.

10 μg of the M13mp19/v-sis single-stranded DNA was annealed with 8 pmol of a phosphorylated oligonucleotide having the sequence (SEQ ID NO: 2):

5'GGTCACAGGCCGTGCAGCTGCCACTGTCTCACAC3'

The sequence is homologous to nucleotides 4283 to 4316 of the v-sis gene using the number system of Devare et al., Proc. Natl. Acad. Sci. USA, Vol. 79, pp. 3179–3182, 1982. The underlined bases of this oligonucleotide denote the change from the v-sis sequence to the human PDGF B sequence. DNA synthesis was initiated on the mutant oligonucleotide, with the complete mutant strand being synthesized with the Klenow fragment of *E. coli* DNA polymerase I using thionucleotide triphosphates, followed by ligation with T4 DNA ligase. Any remaining single-stranded template M13mp19/v-sis DNA was removed by filtration on nitrocellulose filters. The non-mutant strand was nicked by incubation with restriction endonuclease Hind III. The nicked non-mutant strand was then repolymerized with the deoxynucleotide triphosphates, using the mutant strand as a template. As a result, both DNA strands in the final product contained the desired mutations. The DNA was transformed into *E. coli* K12 strain TG1. Plaques were selected, grown in liquid culture, and single-stranded DNA isolated. The DNA was sequenced by the dideoxynucleoside triphosphate method of Sanger et al., *Proc. Natl. Acad. Sci. USA*, 74:5463–5467 (1977), to confirm that the desired mutants had been obtained.
Conversion of Amino Acids 6 and 7
In the next step, the 5' portion of the mutated v-sis gene was replaced with a synthetic DNA fragment which changed amino acids 6 and 7 from the amino acids present at those positions in the v-sis protein to the amino acids in present in human PDGF B. This synthetic fragment also provided a translation-initiating ATG codon immediately preceding the codon for serine 1 of human PDGF B, as well as providing sequences for binding to *E. coli* ribosomes and a restriction site for ligation into the desired *E. coli* expression vector as described below. The synthetic DNA fragment was located to the BglII site located at nucleotide 4061 of the v-sis gene in the numbering system of Devare et al., supra.

Because a BglII site that is present within the M13mp19 vector would complicate and interfere with this step, the mutated v-sis gene was first moved to the commercially available plasmid vector pUC18, which does not contain a BglII site. The M13mp19/v-sis mutant RF DNA was restricted with SalI and BamH1, and the resulting 1193 base pair fragment was isolated by electrophoresis using a low-melting temperature agarose gel. This fragment was ligated to the plasmid pUC18 which had previously also been restricted with SalI and BamH1. The ligated DNA was transformed into commercially available *E. coli* K12 strain DH5 and transformants were selected by growth in the presence of ampicillin. Colonies were selected and grown in liquid culture. Isolated plasmid DNA was analyzed by restriction mapping for the presence of the v-sis insert.

The pUC18/v-sis mutant DNA was restricted with HindIII, which cuts in the polylinker of pUC18 just upstream of the mutated v-sis insert, and with BglII, which cuts within the v-sis DNA at nucleotide 4061 in the numbering system of Devare et al., corresponding to amino acid number 24 of the mature protein product. The large 3565 base pair fragment resulting from this reaction was isolated by electrophoresis in a low-melting temperature agarose gel. This fragment was linked to a synthetic double-stranded DNA fragment with the following sequence (SEQ ID NO: 3):

```
5' AGCTTCTAGAAGGAGGAATAACATATGTCTCTGGGTTCGTTAACCAATTGCG-
3'         AGATCTTCCTCCTTATTGTATACAGAGACCCAAGCAATTGGTAACGC-
-GAACCGGCTATAGATTGCCGAGTGCAAGACACGAACCGAGGTGTTCGA  3'
-CTTGGCCGATACTAACGGCTCACGTTCTGTGTTGGCTCCACAAGCTCTAG    5'
```

This synthetic DNA fragment contains a HindIII "sticky" end at its upstream (left) end and a BglII "sticky" end at its downstream (right) end. In addition, an XbaI site (TCTAGA) is present within the synthetic DNA just downstream of the HindIII "sticky" end, which allows subsequent restriction with XbaI for ligation into the XbaI site of an expression vector, as described below.

The ligated DNA was transformed into *E. coli* K12 strain DH5, with transformants being selected by growth on ampicillin-containing medium. The plasmid DNAs from resulting colonies were analyzed by restriction endonuclease mapping for the presence of the synthetic DNA fragment. At this point, the pUC18/v-sis construction contained a mutated v-sis gene, with amino acid numbers 6, 7, 101, and 107 changed to the amino acids present in human PDGF, and its 5' end altered to begin translation with an ATG codon immediately preceding serine 1.

A small fragment (510 base pairs) between the SmaI and EcoR1 sites, coding for the C-terminal portion of the v-sis protein and a 3'-untranslated sequence, was removed by electrophoresis on a low-melting agarose gel. The large fragment (about 3530 base pairs) was ligated to a synthetic DNA fragment having the following sequence (SEQ ID NO: 4).

```
5'GGGGGGTTCCCAGGAGCAGCGATAAG 3'

3'CCCCCCAAGGGTCCTCGTCGCTATTCTTAA 5'
```

The GGT codon coding for the new glycine residue at position 114 and the TAA termination codon introduced at position 120 are underlined above. The synthetic DNA fragment contains a blunt end at its upstream (left) end for ligating to the blunt end created by restriction of the v-sis mutant sequence with SmaI, and an EcoR1 "sticky" end at its downstream (right) and for ligating to the EcoR1 end created by restriction of the pUC18 polylinker with EcoR1. The ligated DNA was transformed into *E. coli* K12 strain DH5, with transformants being selected by growth on ampicillin-containing medium. The plasmid DNAs from resulting colonies were analyzed for the presence of the synthetic DNA fragment by restriction mapping.

Expression of PDGF $B_{119}$

In the final step, the completed mutated v-sis gene was removed from pUC18 and ligated into the expression vector pCFM1156. The plasmid pCFM1156 was prepared from a known plasmid, pCFM836. The preparation of plasmid pCFM836 is described in U.S. Pat. No. 4,710,473; this patent is hereby incorporated by reference, including relevant portions in the specification, particularly Examples 1 through 7. To prepare pCFM1156 from pCFM836, the two endogenous NdeI restriction sites are cut, the exposed ends are filled with T4 polymerase, and the filled ends are blunt-end ligated.

The resulting plasmid is then digested with ClaI and KpnI and the excised DNA fragment is replaced with a DNA oligonucleotide of the following sequence (SEQ ID NO: 5):

```
              ClaI                                                            KpnI
         5' CGATTTGATTCTAGAAGGAGGAATAACATATGGTTAACGCGTTGGAATTCGGTAC      3'
         3'     TAAACTAAGATCTTCCTCCTTATTGTATACCAATTGCGCAACCTTAAGC     5'
```

Conversion of Amino Acid 114 and Placement of Stop Codon at Amino Acid 120

In the next step, the codon for amino acid number 114 was changed from ACT to GGT, resulting in the substitution of glycine for threonine in the final protein product. In addition, codon number 120, in which GCC codes for alanine in v-sis, was changed to TAA, a translation termination codon. The resulting protein product of this construction ends with the arginine at residue 119. Both of these changes were accomplished in one step by insertion of a synthetic DNA fragment after a SmaI site located within codon number 112.

The pUC18/v-sis mutant DNA generated above was restricted with SmaI, which cuts at nucleotide 4324 in the v-sis sequence in the numbering system of Devare et al., supra, and with EcoR1, which cuts in the polylinker of pUC18 just downstream of the v-sis insert.

The pCFM1156 vector contains a region for insertion of foreign genes between an upstream XbaI site and one of a number of downstream restriction sites. In this case, the downstream EcoR1 site was utilized. The pUC18/v-sis mutant DNA generated above was restricted with XbaI and EcoR1, with the small 383 base pair fragment being isolated by electrophoresis on a low-melting temperature agarose gel. This fragment was ligated to pCFM1156 DNA which had also been restricted with XbaI and EcoR1. The ligated DNA was transformed into *E. coli* K12 strain FM5 (ATCC #67545), with transformants being selected by growth on kanamycin-containing medium. The plasmid DNAs from the resulting colonies were analyzed for the presence of the inserted DNA fragment by restriction mapping.

The final expression plasmid contained an inserted DNA sequence which codes for a protein which begins with an initiating methionine, followed by amino acids 1–119 of the human PDGF B chain sequence. The procaryotic *E. coli* host cells removed the N-terminal methionine after synthesis, so that the final protein produced corresponds to amino acids 1–119 of human PDGF B.

Expression of the 119-amino acid PDGF protein was confirmed by growing bacterial cells containing the expression plasmid at 28°–30° C. until the desired optical density of the culture was reached, and then shifting the culture to growth at 42° C. for several hours. Samples of the cultured cells were taken prior to shifting to 42° C., and at several time points thereafter. It was observed, upon SDS-polyacrylamide gel electrophoretic analysis of the bacterial proteins, that a prominent band of apparent molecular weight 14.6 kd was present in temperature-inducted bacterial cells but not present in cells prior to induction. This protein was present at an approximate level of 25–40 mg per liter of bacterial culture grown to an optical density at 600 nm of 1.0.

Confirmation of Primary Structure of *E. coli* rPDGF $B_{119}$

In order to confirm the expected amino acid sequence and homogeneity of the *E. coli*-produced PDGF $B_{119}$, the recombinant product from three different lots was purified from the inclusion bodies using known techniques, as more fully described in Example 2, and then analyzed by analytical gel electrophoresis and by protein sequencing.

Amino acid sequence analysis was performed by a combination of sequence analysis of the intact rPDGF B, and sequence analysis of tryptic and SV8 protease peptides obtained by digestion of reduced rPDGF B which had been derivatized with 4-vinylpyridine. The sequence determinations were performed using 470A and 477A sequencers (Applied Biosystems, Inc., Foster City, Calif.) This analysis confirmed that the rPDGF $B_{119}$ product from the *E. coli* host cells exhibited the expected sequence, which is shown in FIG. 14.

The purified *E. coli* rPDGF $B_{119}$ from Example 1 was also subjected to SDS-PAGE analysis under both reduced (5% 2-mercaptoethanol with heating) and unreduced (without heating) conditions. Electrophoretic analysis was carried out on a 3 to 27% SDS polyacrylamide gel alongside molecular weight standards obtained from Bio Rad Laboratories (Richmond, Calif.). Protein on the gels was detected after staining with Coomassie Brilliant Blue. At sample loads of 3 to 24 μg, the only bands detected were those attributable to the *E. coli* rPDGF $B_{119}$; a band was observed at approximately 30,000 mw corresponding to a dimer. Upon reduction, a band was observed with an apparent molecular weight of approximately 15,000, corresponding to a monomer.

EXAMPLE 2

Refolding of rPDGF B Chain Homodimer from *E. coli* Inclusion Bodies Using Glutathione as Blocking Agent Approximately 1.5 to 1.6 kg of harvested (i.e., concentrated) *E. coli* paste from Example 1, containing rPDGF $B_{119}$, was removed for refolding. The *E. coli* paste was suspended in 9 volumes (v/w) of 20 nM disodium ethylenediaminetetraacetic acid (EDTA), with the temperature being maintained at 4° C. The suspended cell paste was lysed using a Manton-Gaulin homogenizer at a pressure of 14,000 psi and a temperature of 12° C. The lysate was immediately centrifuged at 3,600×C for 60 minutes at 4° C. and the supernatant discarded, with the inclusion body rPDGF-containing pellet being saved.

The pellet was suspended in 14 volumes (v/w) of 8.5M urea, 0.1M glycine, pH 3.0, and stirred for 30 minutes. Meanwhile, SE-Sepharose® (Pharmacia, Uppsala, Sweden) chromatography resin was drained by placing the commercially available resin in a sintered glass funnel, allowing the resin to drain by gravity, washing the resin with deionized water, and allowing the resin to drain once again. With continued stirring of the resuspended pellet, 2.4 kg of the drained resin was added to the pellet suspension. Stirring was stopped after 30 minutes. The resin was allowed to settle and the supernatant discarded. Five liters of 8.5M urea, 0.1M glycine, pH 3.5, was added to the settled resin. The mixture was stirred for an additional five minutes, with the resin again being allowed to settle, and the supernatant being discarded.

Five liters of 8.5M urea, 20 nM phosphoric acid, pH 3.0, were then added to then added to the resin. The resulting mixture was again stirred for five minutes, with the resin again being allowed to settle and the supernatant being discarded. A second 5-liter volume of 8.5M urea, 20 nM phosphoric acid, pH 3.0 was added to the settled resin. This mixture, with stirring, was subjected to a vacuum equal to 25 inches of mercury for 30 minutes. The vacuum was then broken and the mixture was made 5 nM in dithiothreitol (DTT), with the pH being adjusted to 7.7 with 10M sodium hydroxide (NaOH).

The vacuum was restored and the mixture stirred for 30 minutes. Still under vacuum, with stirring discontinued, the resin was allowed to settle and 90% of the supernatant discarded. The resin was immediately slurried with the residual liquid and poured into a 25-cm-diameter column (batch column), a flow adapter attached, and the resin packed at 100 cm/hour for 10 minutes with 8.5M urea, 20 nM sodium phosphate ($Na_2HPO_4$), pH 7.7 that had been and was being sparged with $N_2$ gas (Buffer A). The flow adapter was lowered to the surface of the resin and the column was washed with additional buffer A at a flow rate of 25 cm/hour until the effluent absorbance at 280 nm was constant.

The outlet of the batch column was then connected to the inlet of a second 25 cm×20 cm column (resolving column) packed with fresh SE-Sepharose® (Pharmacia) and equilibrated with buffer A. The batch and resolving columns were then resolved at a flow rate of 25 cm/hour with an 80-liter linear gradient from 100% buffer A to 100% buffer B (8.5M urea, 20 nM $Na_2HPO_4$, 0.4M NaCl, pH 7.7) which had been and was being sparged with $N_2$ gas. The appropriate fractions were immediately pooled and placed under vacuum as they came off the column. The yield was between 0.45 and 0.90 gm per liter of fermentation broth.

The denatured rPDGF $B_{119}$-containing solution was diluted, if necessary, to an absorbance of between 0.4 and 0.5 OD. The monomeric protein solution was then made 0.1M in oxidized glutathione and the pH adjusted to 8.0 with 10M NaOH. The solution was again placed under vacuum and stirred for 18 to 24 hours. The vacuum was broken and the pH of the now derivatized monomeric rPDGF mixed disulfide intermediate was lowered to 3.0 with HCl. The resultant solution was concentrated to ½ its initial volume, and then diafiltered first against four volumes of 8.5M urea, 0.1M acetic acid, and then followed by four volumes of 0.1M acetic acid using an Amicon® YM 10 (Amicon Inc., Danvers, Mass.) ultrafiltration membrane. The final protein concentration was between 1.5 and 2.0 mg/mL ($K_{1\%280\ nm}$=0.46) with rPDGF-S-S-G purity >85%, and a yield of between 0.45 and 0.90 gm per liter of fermentation broth.

Refolding was effected by dilution of the rPDGF-S-S-G solution to 0.1 mg/mL with 20 mM Tris. Subsequently, 1M cysteine in 0.1M acetic acid was added to this solution, to a final concentration of 1 mM, and the pH adjusted to 8.0 with NaOH. The solution was stirred for 16 hours in order to unblock the derivatized monomeric rPDGF-S-S-G intermediate and initiate formation of intrachain and interchain disulfide bonds of the desired dimeric end product, and then made 0.1M in acetic acid. The yield was 0.32 to 0.63 g per liter of fermentation broth.

The refolded dimeric rPDGF solution was loaded, at a flow rate of 100 cm/hr, onto a 11.3×5 cm column of controlled pore glass (CPG, pg-350–400 96 $M^2$/g, 382 Åmean diameter, Signal Chemical Company, St. Louis, Mo.), equilibrated in either 0.5M glycine, pH 3.5 (Buffer C) or 0.05M glycine, 0.4M NaCl, pH 3.5 (buffer D). Following the loading of the rPDGF post-oxidation solution onto the column, the column was washed with the equilibration buffer at a flow rate of 40 cm/hour. The purified rPDGF $B_{119}$ homodimer was then eluted from the column, again at a flow rate of 40 cm/hr, by the application of a 5 liter gradient starting with either buffer C or D and finishing with either 2M guanidinium chloride in buffer C or 8M urea in buffer D. The appropriate fractions of pure rPDGF $B_{119}$ homodimer were pooled. The yield was between 0.25 and 0.5 g per liter of fermentation broth.

EXAMPLE 3

Corneal Reepithelialization

Example 3 evaluates the ability of a substance to enhance the rate of corneal epithelial mitosis and migration as a surface defect is closed. These results are indicative of the efficacy of PDGF when used in non-healing corneal ulcers or abrasions.

New Zealand Albino (NZA) rabbits were anesthetized systemically using 6 mg/kg of ketamine and 30 mg/kg of xylazine administered by subcutaneous injection. Topical ophthalmic anesthesia was also performed with one drop of proparacaine (Opthetic). The entire corneal epithelium was gently removed using a corneal Gil knife. Care was taken to insure that the basement membrane was not compromised. Fifty microliters of sodium fluorescein was instilled into the eye to stain the defect, and the wound was photographed with a slit lamp equipped with a cobalt blue exciter filter. The rabbit eyes were dosed with 50 µl of PDGF at 100 µg/ml at 2 hours, 8 hours and 24 hours after surgery. The PDGF used was the rPDGF $B_{1,9}$ prepared in Example 2, above. The wound was photographed at intervals up to 84 hours after surgery, and the photographs of the eyes were subjected to computer image analysis to determine the area of the wound to generate a "healing curve" that represents the percent of the wound area remaining. The smaller this percentage, the greater is the degree of healing that has occurred.

Figure 2:
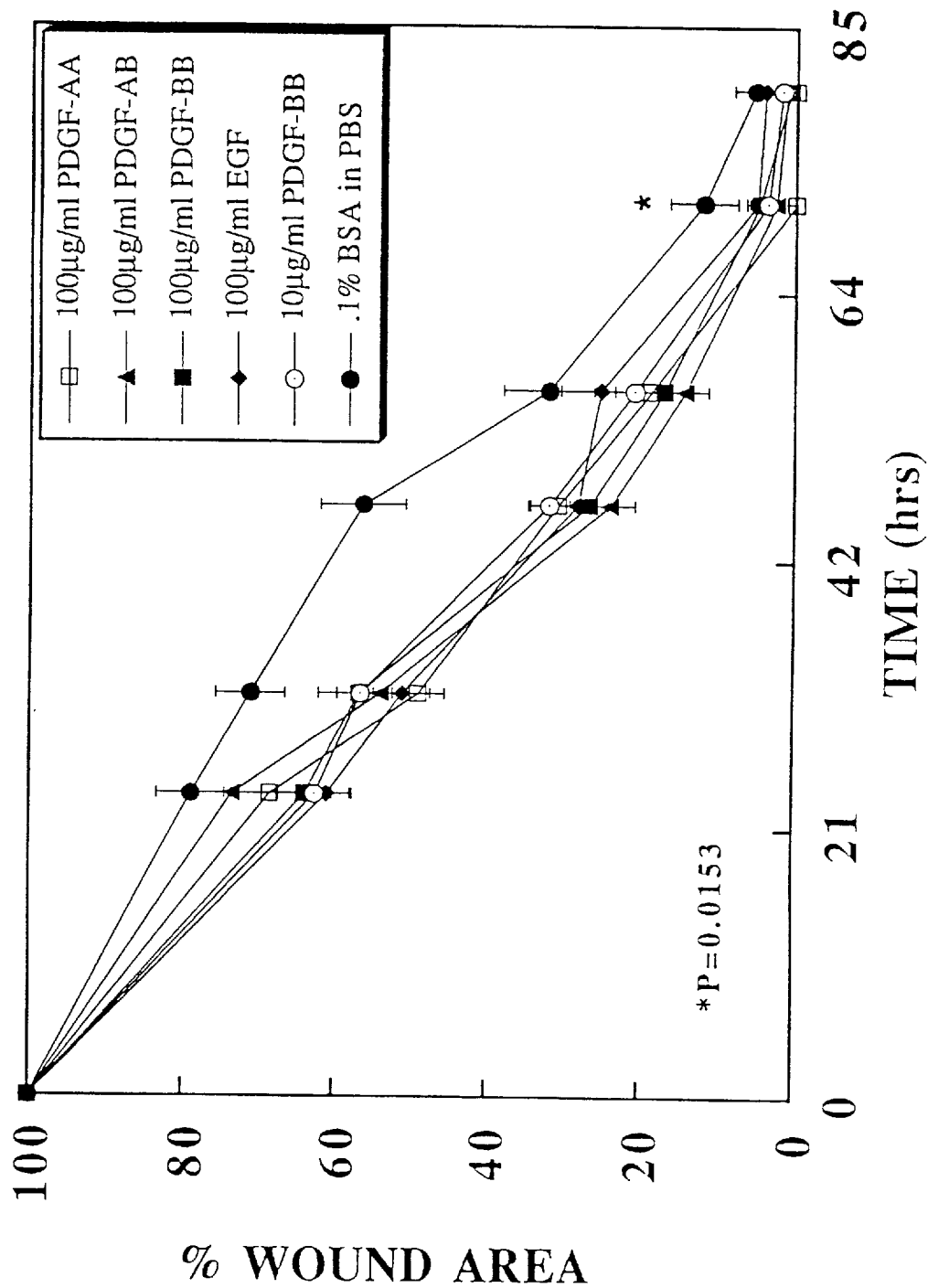
FIG. 2 is a graph showing the results of growth factor treatment, including various forms of PDGF and EGF, in promoting corneal reepithelialization, in which the percentage of the wound area remaining is plotted against time (PBS=phosphate buffered saline control (no growth factor))
Figure 3:
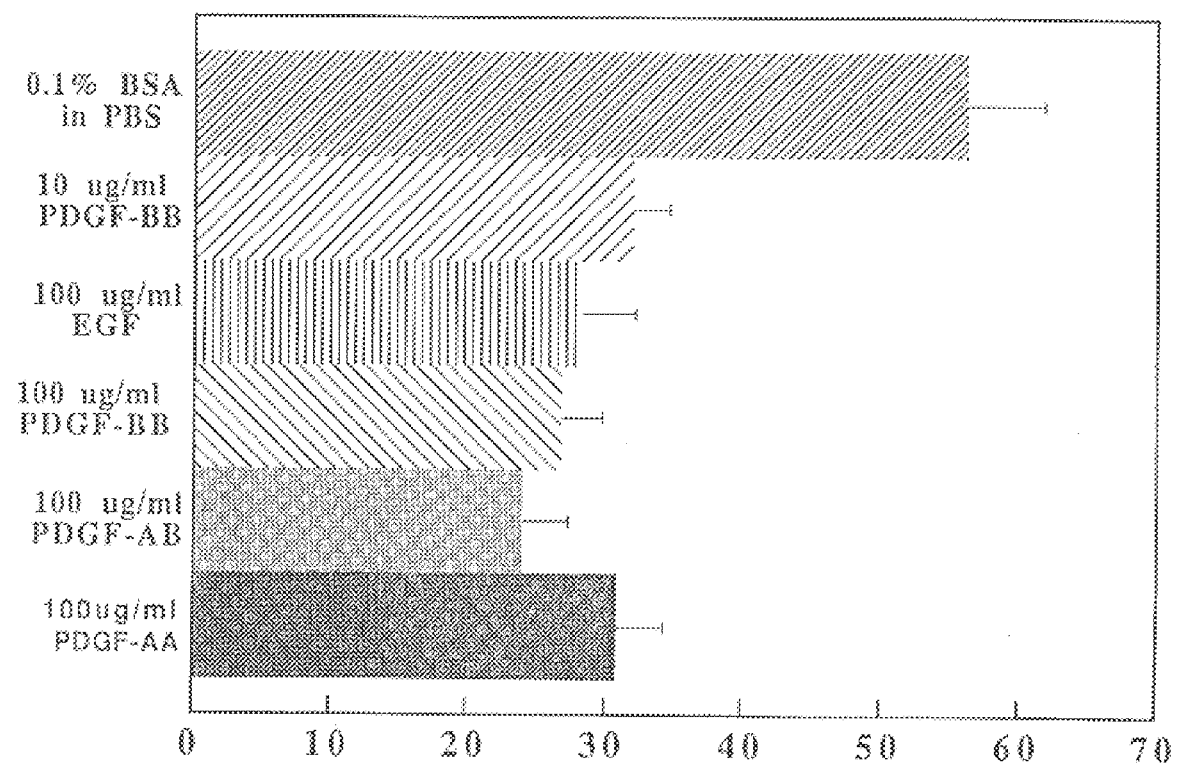
FIG. 3 is a bar graph depicting the results of FIG. 2 at 71 hours following the initial surgery.
Figure 4:
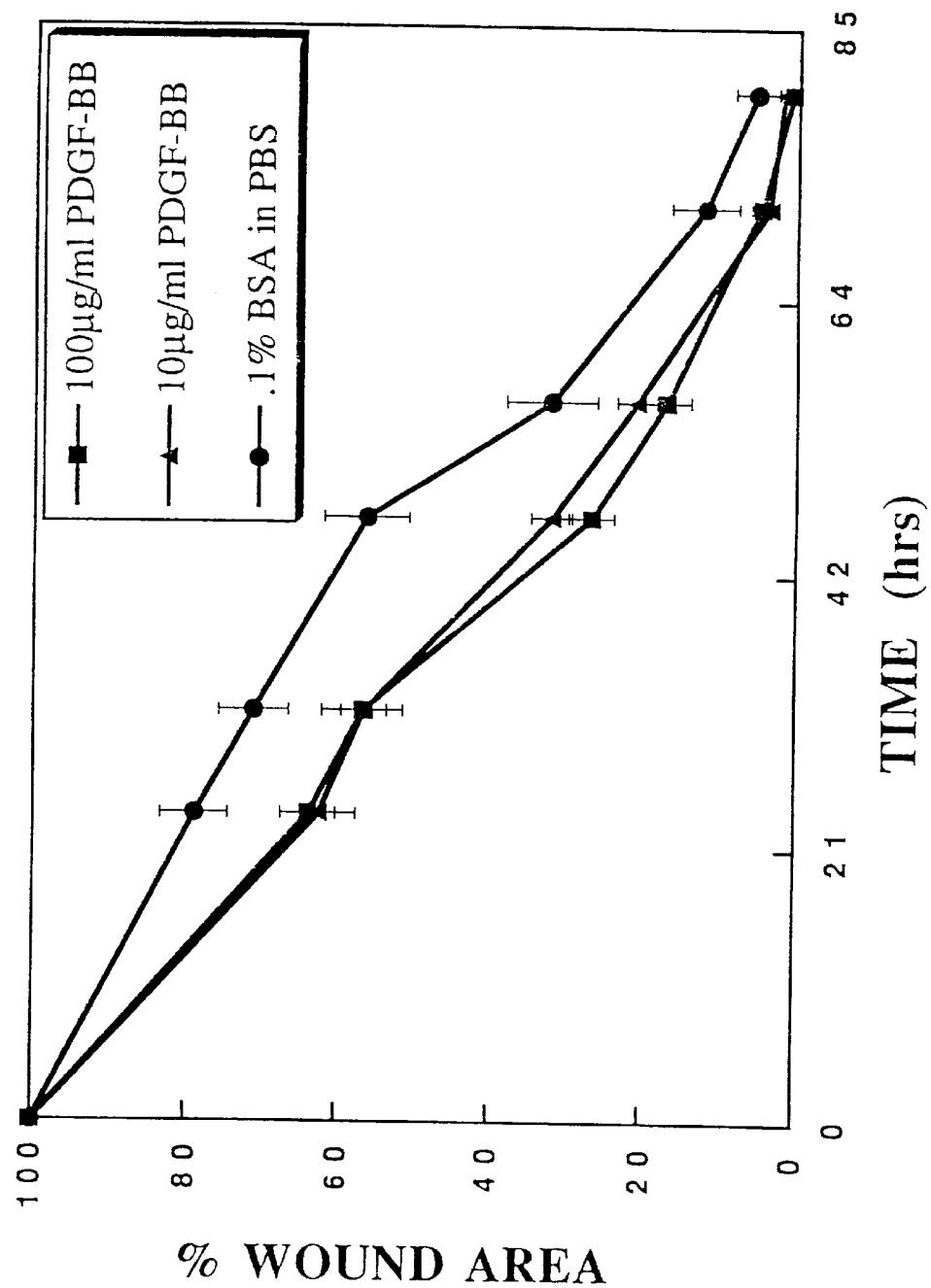
FIG. 4 is a graph showing the results of treatment with the BB isoform of PDGF at 100 $\mu$g/ml and 10 $\mu$g/ml in promoting corneal reepithelialization, as in FIG. 2.
Figure 5:
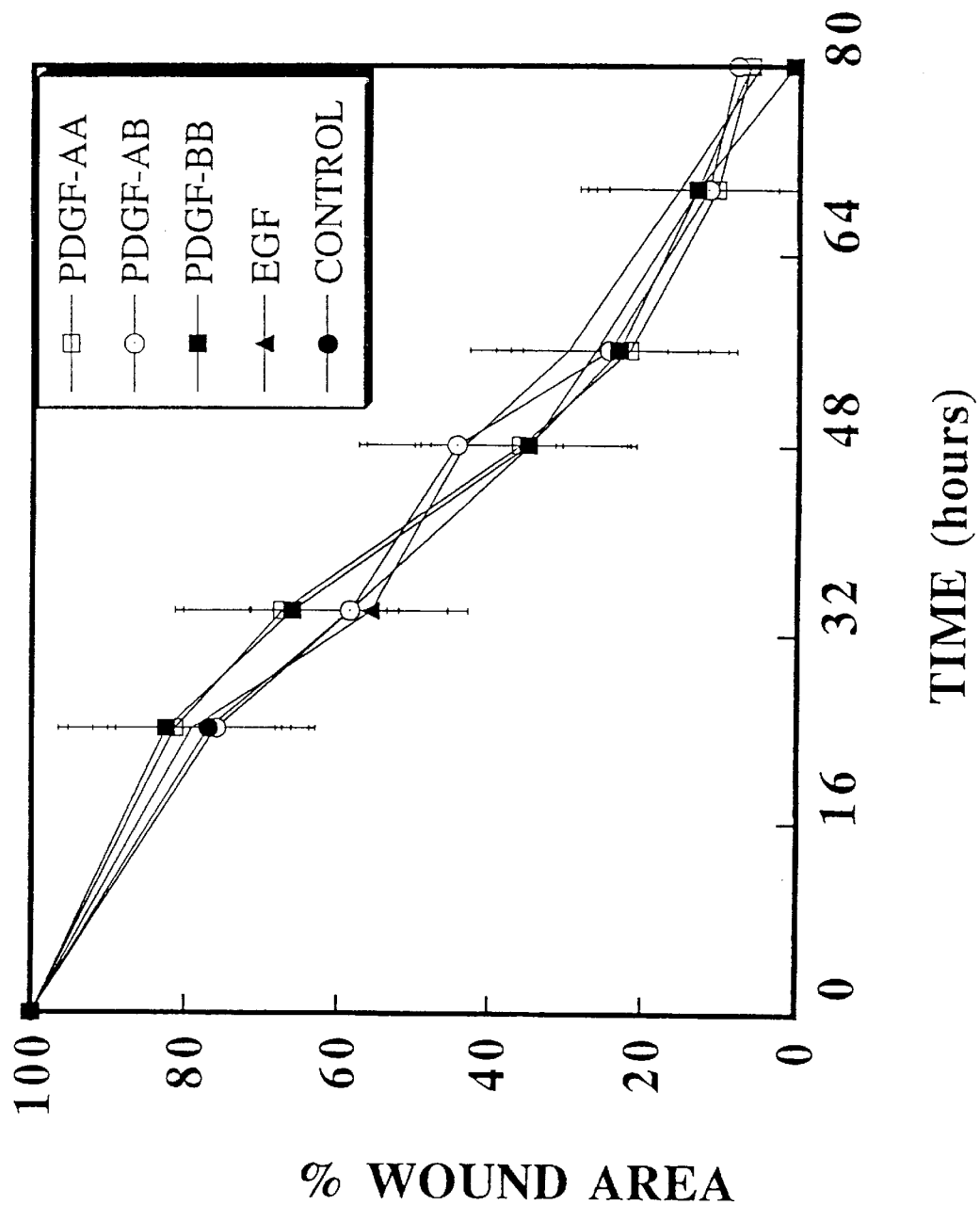
FIG. 5 is a graph showing the results of treatment with 10 $\mu$g/ml of various isoforms of PDGF or EGF in promoting corneal reepithelialization, as in FIG. 2.

The results are shown in FIGS. 2 through 5. At 100 µg/ml PDGF, an increase in the rate of healing detectable by 24 hours and continuing until wound closure was seen. (FIG. 2 and FIG. 3). The BB homodimer of PDGF appeared somewhat more effective than the other two isoforms in this study. (FIG. 3). At 10 µg/ml, the effect was variable, and some experiments showed substantial wound healing activity of the BB isoform of PDGF (FIG. 4), while other experiments showed little or no effect of any of the PDGF isoforms at that low concentration (FIG. 5). The conclusion from the experimental results at low dosages (FIGS. 4 and 5) is that the BB isoform of PDGF at 10 µg/ml had either no effect or an enhancement of the rate of corneal epithelial wound healing. The results varied in individual experiments. It may be possible to correlate these results with the level of inflammation present on the ocular surface after surgery. The rate of proteolysis and inflammation of the PDGF peptide would be increased in a more inflamed eye.

EXAMPLE 4

Healing After Anterior Keratectomy

The experiments of Example 4 evaluate the ability of the epithelium to heal without the presence of a basement membrane. In the clinical situation this may be indicative of healing after a bacterial corneal ulcer where the ulcer itself has invaded the corneal stroma. Also, this type of healing occurs after clinical keratectomy. The anterior keratectomy is a more severe test of corneal healing because the epithelial cells must migrate across the stromal collagen while forming a basement membrane and proliferating.

Rabbits were anesthetized as in Example 3. A 6.0 mm shielded corneal trephine was used to mark the corneal surface and outline an area bound to mid-corneal depth. Using a platformed forceps, the portion of the epithelium and anterior stroma within the marked area was removed along a stromal lamellar boundary. Dosing and wound evaluation were performed using the same techniques as in the corneal reepithelialization experiments (Example 3). The PDGF used was the rPDGF $B_{119}$ prepared in Example 2, above.

Figure 6:
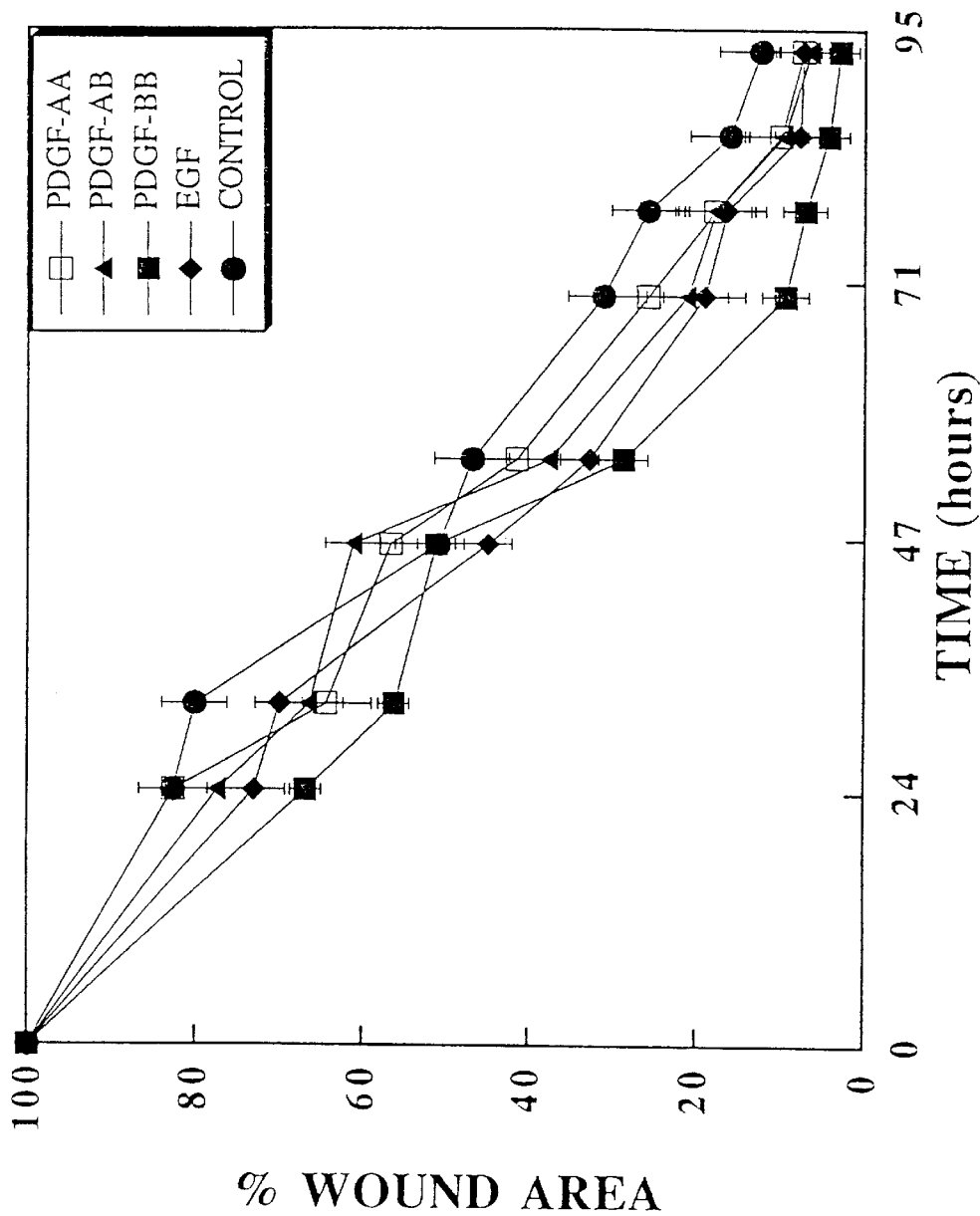
FIG. 6 is a graph showing the results of treatment with various isoforms of PDGF and EGF in promoting healing after anterior keratectomy, in which the percentage of the wound area remaining is plotted against time.
Figure 7:
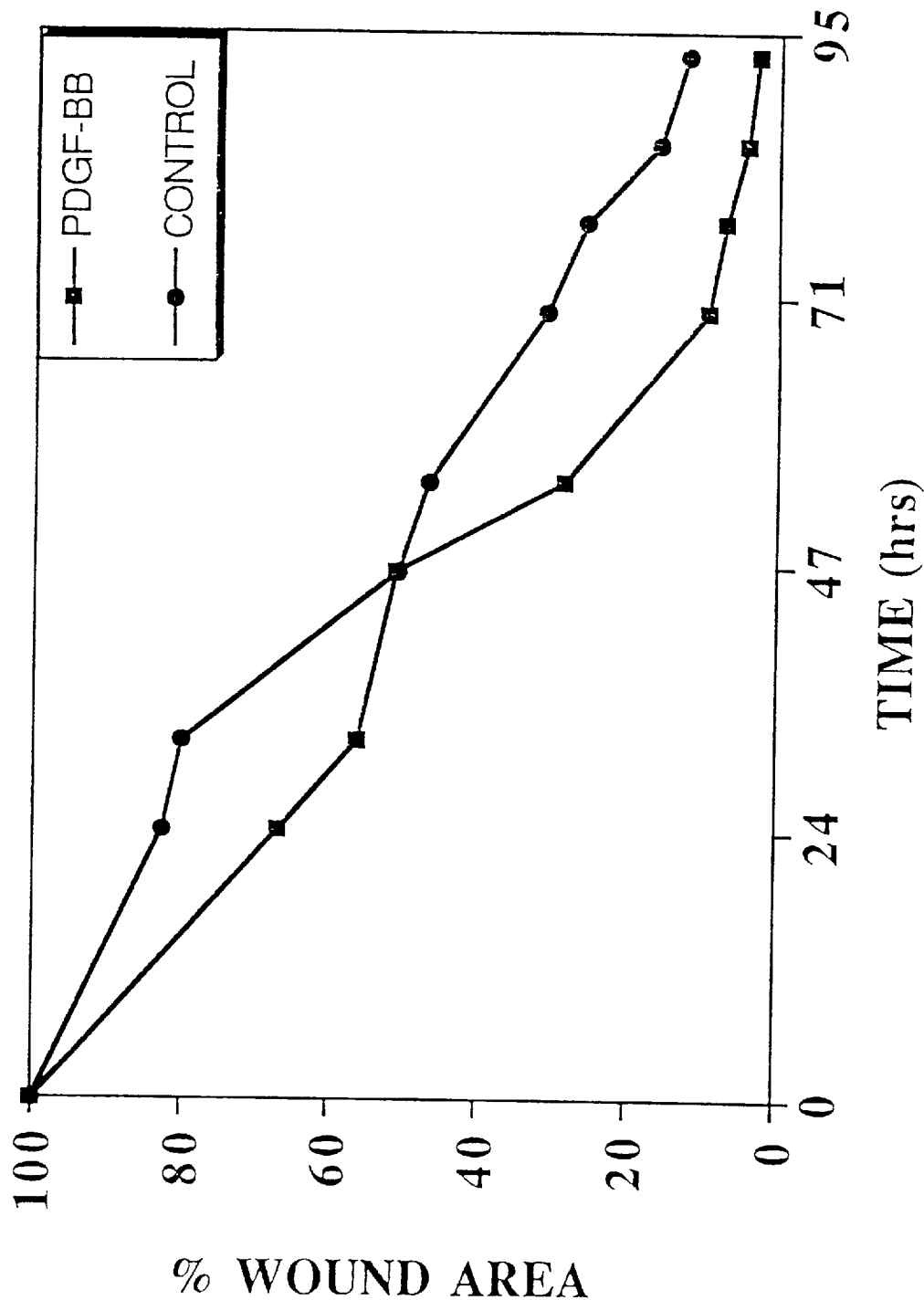
FIG. 7 is a similar graph depicting the results of treatment with the BB isoform of PDGF at 100 $\mu$g/ml in promoting healing after anterior keratectomy.
Figure 8:
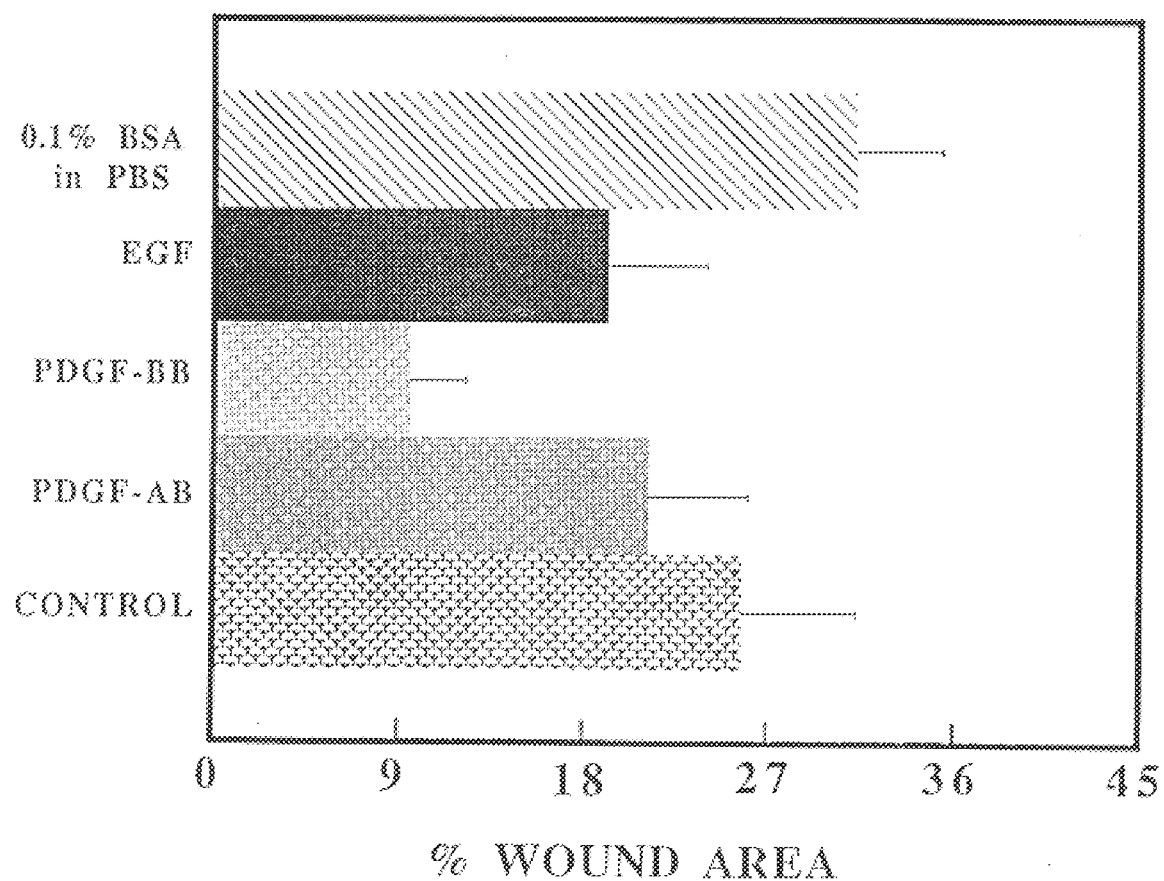
FIG. 8 is a bar graph depicting the results of FIG. 6 at 71 hours following the initial surgery.

The results are shown in FIGS. 6, 7, and 8. At 100 µg/ml, all of the growth factor groups (AA, AB and BB isoforms of PDGF and EGF) healed faster than the control (0.1% bovine serum albumin in phosphate buffeted saline, FIGS. 6 and 7). The BB isoform of PDGF showed the most dramatic increase in healing both visually on examining the eyes as well as graphically as can be seen in the bar graph of the 71 hour time point (FIG. 8).

EXAMPLE 5

Tensile Strength Experiments

The tensile strength experiments of Example 5 evaluate the effects of substances on the healing of the corneal stroma. The stroma composes a central 89% of the corneal thickness and is made up of type I collagen lamellae with fibrils separated in a regular array by less than ½ the wavelength of light. These fibrils are surrounded by glycosaminoglycan ground substance. This is important to confer transparency to the cornea as well to provide the majority of corneal structural strength. The clinical importance of these techniques is if they are indicative of healing after intra-ocular surgery (i.e., cataract), while refractive surgery, as well as corneal trauma.

Rabbits were anesthetized as in Example 3. For the tensile strength tests, a 9.0 mm incision was placed at from 12:00 to 6:00 in the central cornea. The incision was closed with four interrupted 10.0 nylon sutures. The eye was dosed with 50 µl of test solution at 2 hours, 8 hours and 24 hours after therapy. The PDGF used in the test solution was the rPDGF $B_{119}$ prepared in Example 2, above. At the end of the healing period, 21 days, the rabbit was sacrificed and the cornea was isolated. A 4.0 mm strip was cut from the central cornea perpendicular to the incision. The tissue strip was then clamped into an Instron materials testing machine and the force of "stress" required to pull the tissue apart was measured. The increase in force applied by the machine was ramped up using a computer program. Therefore, in the first study both the force required to pull the incision apart and the time it took to do this was recorded.

In the second study a comparison was made between PDGF, EGF, and control. In this study, the force required to pull the incision apart was expressed as a "stress sum" as a percent of control. The ability of the cornea to deform before the incision fails is called "strain sum" and is also expressed as a percentage of the control. The "strain sum" is thought to be indicative of the presence of glycosaminoglycans, the ground substance of the stroma.

Figure 9:
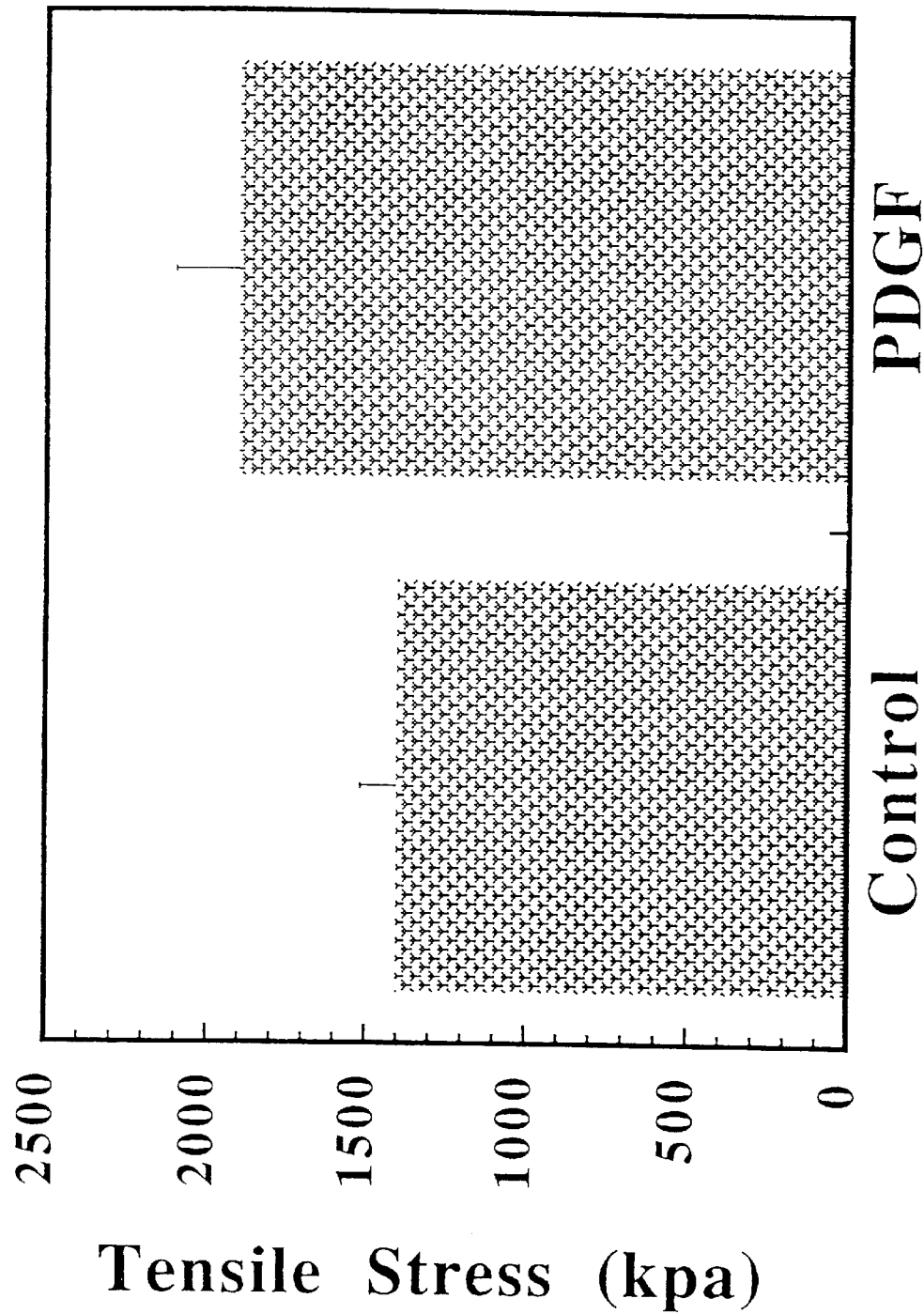
FIG. 9 is a bar graph depicting the results of PDGF treatment in increasing tensile strength in corneas.
Figure 10:
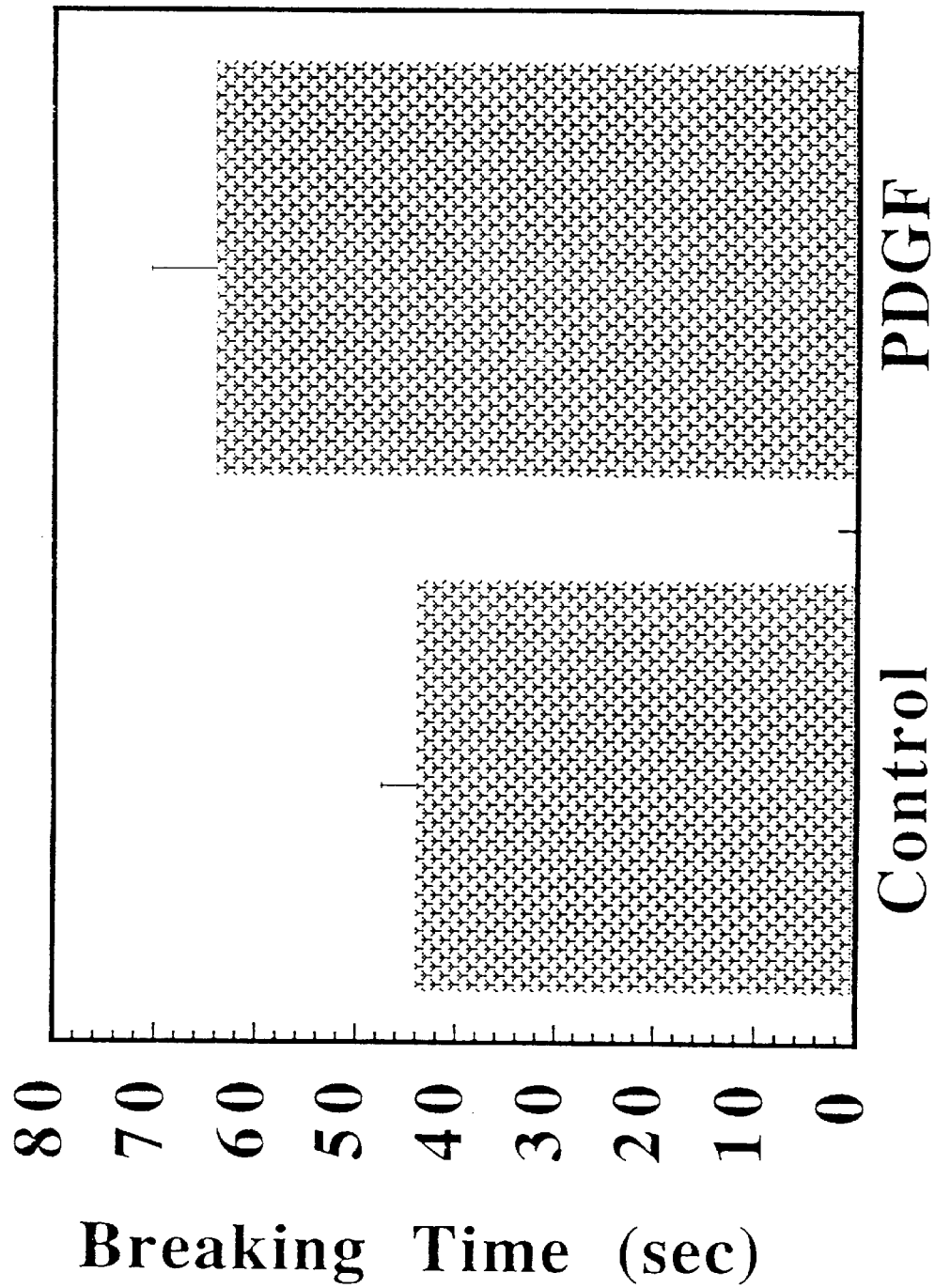
FIG. 10 is a bar graph depicting the results of PDGF treatment in increasing the breaking time of corneal tissue, another measure of the tensile strength of the cornea.
Figure 11:
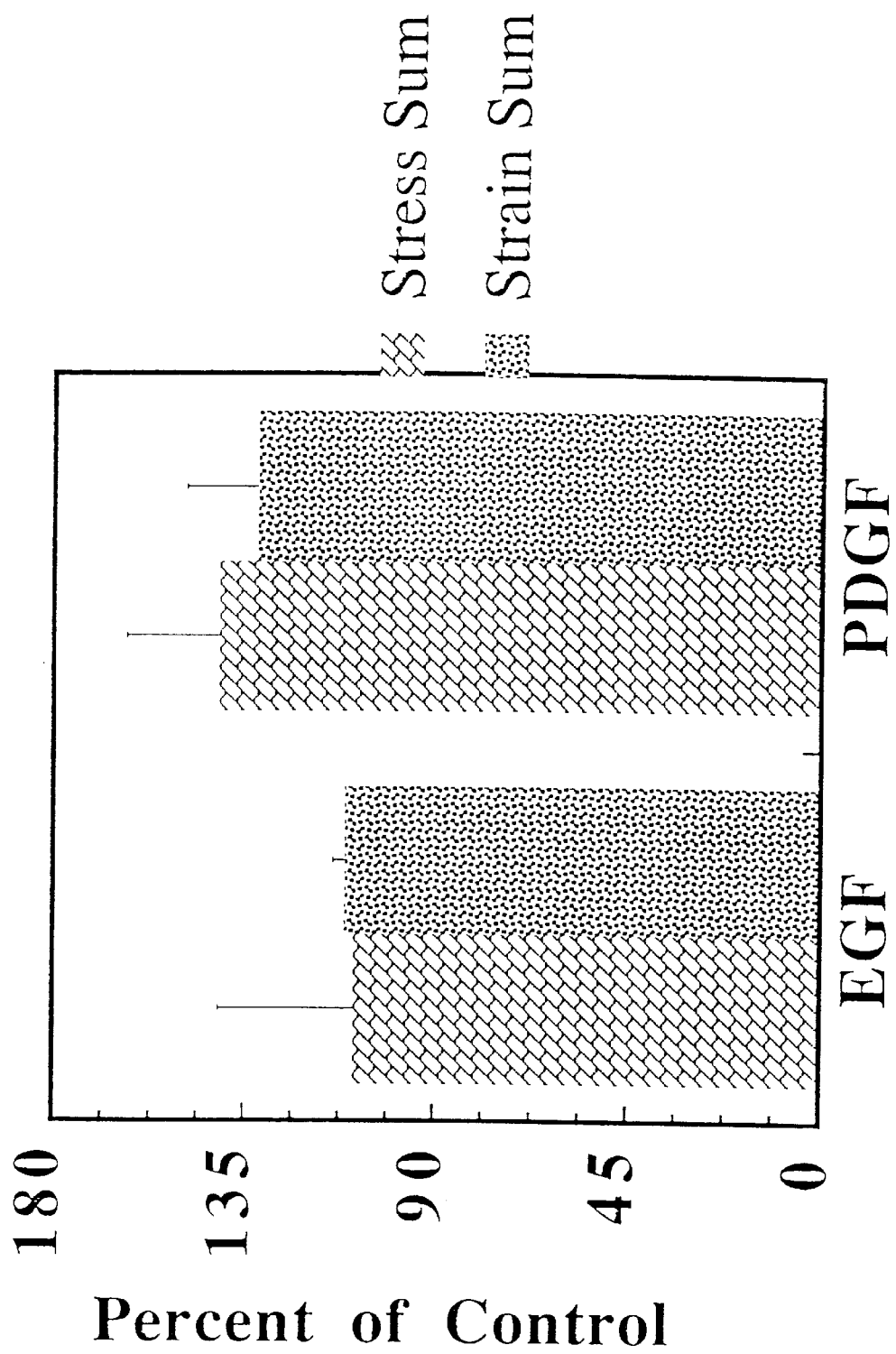
FIG. 11 is a bar graph depicting the results of PDGF and EGF treatment in increasing the ability of corneal tissue to withstand stress and strain.

The results of the tensile strength experiments are shown in FIGS. 9–11. Both studies show that there is an increase in corneal and incision strength for the PDGF-treated cornea versus the control. In the first study there was a 36% increase in the tensile strength required (FIG. 9) and a 50% increase in the breaking time (FIG. 10).

In addition, the second experiment indicated that PDGF treatment resulted in a 32% greater wound strength than EGF treatment. The PDGF-treated cornea also exhibited a 30% greater ability to withstand strain than the EGF-treated cornea (FIG. 11).

Figure 12A:
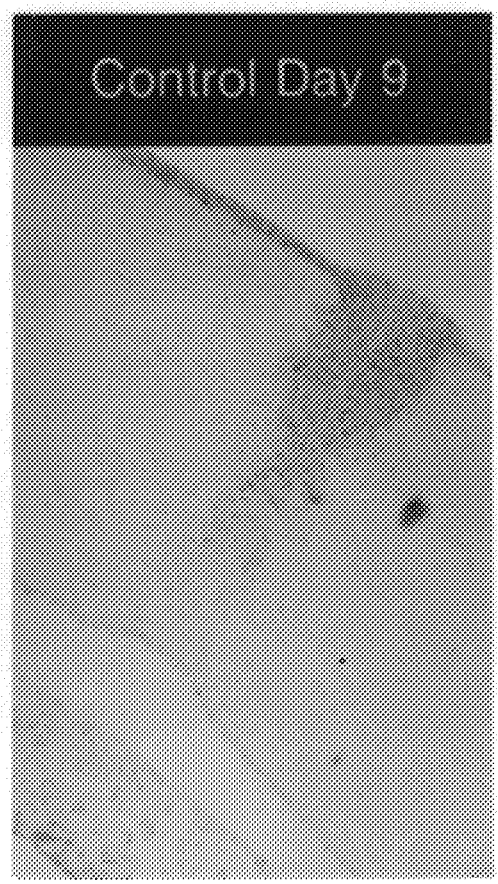
FIG. 12A is a light photomicrograph of a section of control cornea nine days after surgery.
Figure 12B:
FIG. 12B is a light photomicrograph of a section of cornea nine days after surgery that had been dosed three times after the first 24 hours after surgery with 100 $\mu$g/ml of the BB isoform of PDGF.

Light micrographs of corneas from these studies are shown in FIGS. 12A and 12B. FIG. 12A is a light micrograph of a section of a control cornea, nine days after incision. The corneal epithelium has thickened and formed a plug into the incision. Few activated keratocytes are seen in this section. This is indicative of an early stage of wound healing.

FIG. 12B is a light micrograph of a section of a cornea nine days after surgery which was dosed three times over the first 24 hours after surgery with 100 μg/ml of the BB isoform of PDGF. The epithelial plug has been displaced to the surface and the incision area is filled with large numbers of activated keratocytes, This is indicative of a much further advanced stage of wound healing, showing the effectiveness of PDGF in advancing the course of wound healing when applied shortly after surgery, by both accelerating the rate of healing and improving the quality of healing.

EXAMPLE 6

Gel Contraction Assay

The gel contraction assay of Example 6 is an in vitro assay to determine the effects of a substance on activating fibroblasts to cause collagen contraction. This type of interaction may be indicative of activity within the corneal stroma.

In the performance of this assay, a tissue culture well was coated on the bottom with agarose. A mixture of type 1 collagen and fibroblasts was placed on the agarose surface. This mixture was allowed to form a matrix. The medium on top of the matrix was supplemented with the test substance (PDGF at from 0.01 to 100 mg/ml). The PDGF used was the rPDGF $B_{119}$ prepared in Example 2, above. At two time points (3 days and 6 days), the retraction of the collagen matrix away from the wall of the well was measured by determination of the residual gel or matrix area.

Figure 13:
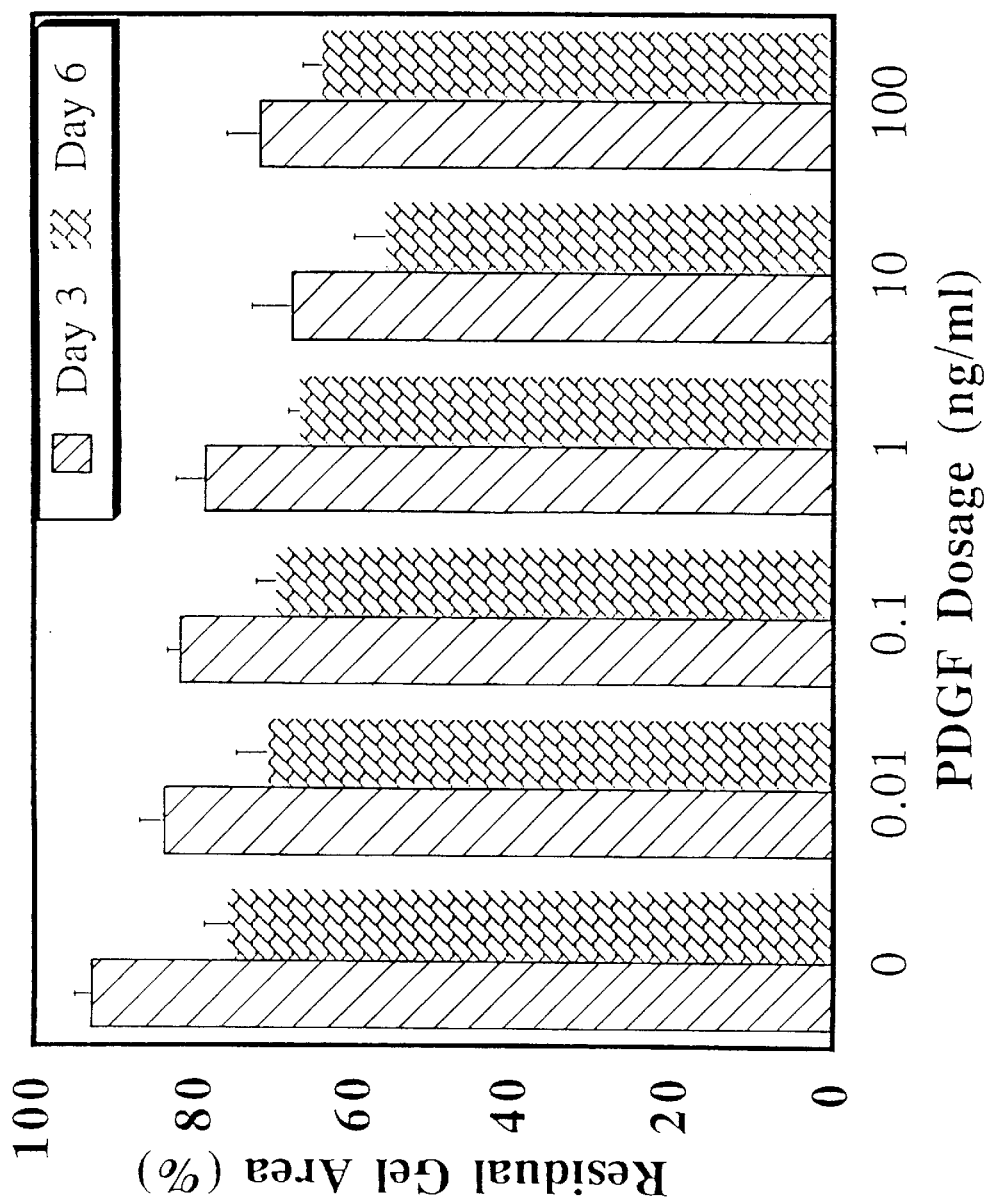
FIG. 13 is a bar graph depicting the results of treatment with various doses of PDGF in an in vitro gel contraction assay to determine the effects of PDGF on activating fibroblasts to cause collagen contraction.

The results are shown in FIG. 13. There was a dose-response relationship between the dose of PDGF and the amount of concentration at days 3 and 6, up to a dose of 10 mg/ml. At 100 mg/ml, the effect was slightly less than at 10 mg/ml, possibly indicating saturation of the receptors.

This assay indicates activation of fibroblasts to cause collagen contraction within the corneal stroma.

ADVANTAGES OF THE INVENTION

The method of accelerating corneal wound healing according to the present invention is effective in accelerating clinically detectable healing through proliferation and activation of epithelial cells and/or keratocytes of the cornea. The method requires relatively few components and is easy to perform. Most significantly, the method promotes re-innervation of the corneal epithelium, a critical factor in restoring corneal function and structure. The method is effective in both healing of corneal surface defects in the presence of a basement membrane and the healing of the corneal epithelium in the absence of a basement membrane, as well as promoting the healing of the corneal stroma after intra-ocular surgery, penetrating keratoplasty, refractive surgery, or corneal trauma. The method is also effective for treatment of non-traumatic pathological lesions of the cornea, such as non-healing corneal ulcers caused by diabetes. The method is compatible with other corneal or intra-ocular treatments used after surgery.

The examples cited herein demonstrate the effectiveness of PDGF in accelerating wound healing even though corneal epithelium in its normal state was not known to possess receptors specific for PDGF. This is an indication of unexpected results resulting from the use of PDGF to stimulate corneal wound healing.

Although the present invention has been described in considerable detail with reference to certain preferred versions thereof, other versions are possible. Therefore the spirit and scope of the appended claims should not be limited to the description of the preferred versions contained herein.

We claim:

1. A method of accelerating corneal wound healing in a mammal having a wound that penetrates the corneal anterior stroma, comprising:

identifying a mammal having a wound that penetrates the corneal anterior stroma;

providing an ophthalmically compatible solution of platelet-derived growth factor; and applying the solution to the wound of the mammal at the time of or subsequent to occurrence of the wound in a quantity sufficient to accelerate clinically detectable healing thereof.

2. The method of claim 1 wherein the platelet-derived growth factor is selected from the group consisting of the AA isoform, the AB isoform, the BB isoform, and mixtures thereof.

3. The method of claim 2 wherein the platelet-derived growth factor is the BB isoform.

4. The method of claim 1 wherein the concentration of platelet-derived growth factor in the solution is from about 10 µg/ml to about 1000 µg/ml.

5. The method of claim 4 wherein the concentration of platelet-derived growth factor in the solution is from about 50 µg/ml to about 500 µg/ml.

6. The method of claim 5 wherein the concentration of platelet-derived growth factor in the solution is about 100 µg/ml.

7. The method of claim 1 wherein the platelet-derived growth factor is a recombinantly-derived refolded B-chain homodimer of 119 amino acids, having the amino acid sequence of SEQ ID NO: 1.

8. The method of claim 1 wherein the solution is applied once or more to the cornea subsequent to occurrence of the corneal wound.

9. The method of claim 8 wherein the solution is applied from once to three times to the cornea.

10. The method of claim 9 wherein the solution is applied at about 2 hours, at about 8 hours, and at about 24 hours after occurrence of the wound.

11. The method of claim 1 wherein the solution is applied once or more to the cornea at the time of occurrence of the corneal wound.

12. The method of claim 1 wherein the wound results from the effects of a surgical laser.

13. The method of claim 1 wherein the wound is a consequence of diabetes.

14. A method of accelerating corneal wound healing in a mammal having a corneal wound that penetrates the corneal anterior stroma comprising:

(a) providing an ophthalmically compatible solution of BB isoform of platelet-derived growth factor; and (b) applying the solution to the cornea of the mammal at the time of or subsequent to occurrence of the wound in a quantity sufficient to accelerate clinically detectable healing thereof.

15. A method of accelerating corneal wound healing in a mammal having a corneal wound that penetrates the corneal anterior stroma comprising:

(a) providing an ophthalmically compatible solution of a recombinantly derived refolded B-chain homodimer of 119 amino acid, having the amino acid sequence of SEQ ID NO:1; and (b) applying the solution to the cornea of the mammal at the time of or subsequent to occurrence of the wound in a quantity sufficient to accelerate clinically detectable healing thereof.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH:119 amino acid residues
        ( B ) TYPE:amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:1:

| | | | | | | | | | | |
|---|---|---|---|---|---|---|---|---|---|---|
|Ser|Leu|Gly|Ser|Leu|Thr|Ile|Ala|Glu|Pro|Ala|Met|
| | | | |5| | | | |10| | |
|Ile|Ala|Glu|Cys|Lys|Thr|Arg|Thr|Glu|Val|Phe|Glu|
| | |15| | | | |20| | | | |
|Ile|Ser|Arg|Arg|Leu|Ile|Asp|Arg|Thr|Asn|Ala|Asn|
|25| | | | |30| | | | |35| |
|Phe|Leu|Val|Trp|Pro|Pro|Cys|Val|Glu|Val|Gln|Arg|
| | | |40| | | | |45| | | |
|Cys|Ser|Gly|Cys|Cys|Asn|Asn|Arg|Asn|Val|Gln|Cys|
| |50| | | | |55| | | | |60|
|Arg|Pro|Thr|Gln|Val|Gln|Leu|Arg|Pro|Val|Gln|Val|
| | | | |65| | | | |70| | |
|Arg|Lys|Ile|Glu|Ile|Val|Arg|Lys|Lys|Pro|Ile|Phe|
| | |75| | | | |80| | | | |
|Lys|Lys|Ala|Thr|Val|Thr|Leu|Glu|Asp|His|Leu|Ala|
|85| | | | |90| | | | |95| |
|Cys|Lys|Cys|Glu|Thr|Val|Ala|Ala|Ala|Arg|Pro|Val|
| | | |100| | | | |105| | | |
|Thr|Arg|Ser|Pro|Gly|Gly|Ser|Gln|Glu|Gln|Arg| |
| | |110| | | | |115| | |119| |

( 2 ) INFORMATION FOR SEQ ID NO: 2:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

```
GGTCACAGGC CGTGCAGCTG CCACTGTCTC ACAC                           34
```

( 2 ) INFORMATION FOR SEQ ID NO: 3:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 3:

```
AGCTTCTAGA AGGAGGAATA ACATATGTCT CTGGGTTCGT                     40

TAACCATTGC GGAACCGGCT ATGATTGCCG AGTGCAAGAC                     80

ACGAACCGAG GTGTTCGA                                             98
```

( 2 ) INFORMATION FOR SEQ ID NO: 4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO: 4:

```
CCCCCCAAGG GTCCTCGTCG CTATTCTTAA                                30
```

( 2 ) INFORMATION FOR SEQ ID NO: 5:

( i ) SEQUENCE CHARACTERISTICS:
    ( A ) LENGTH: 55 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO: 5:

```
CGATTTGATT  CTAGAAGGAG  GAATAACATA  TGGTTAACGC                40

GTTGGAATTC  GGTAC                                             55
```

( 2 ) INFORMATION FOR SEQ ID NO: 6:

( i ) SEQUENCE CHARACTERISTICS:
    ( A ) LENGTH: 386 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO: 6:

```
CTAGAAGGAG  GAATAACAT ATG TCT CTG GGT TCG TTA ACC             40
                     Met Ser Leu Gly Ser Leu Thr
                                      5

ATT GCG GAA CCG GCT ATG ATT GCC GAG TGC AAG ACA               76
Ile Ala Glu Pro Ala Met Ile Ala Glu Cys Lys Thr
         10                  15

CGA ACC GAG GTG TTC GAG ATC TCC CGG CGC CTC ATC               112
Arg Thr Glu Val Phe Glu Ile Ser Arg Arg Leu Ile
 20              25                      30

GAC CGC ACC AAT GCC AAC TTC CTG GTG TGG CCG CCC               148
Asp Arg Thr Asn Ala Asn Phe Leu Val Trp Pro Pro
             35              40

TGC GTG GAG GTG CAG CGC TGC TCC GGC TGT TGC AAC               184
Cys Val Glu Val Gln Arg Cys Ser Gly Cys Cys Asn
     45              50                      55

AAC CGC AAC GTG CAG TGC CGG CCC ACC CAG GTG CAG               220
Asn Arg Asn Val Gln Cys Arg Pro Thr Gln Val Gln
                 60                  65

CTG CGG CCA GTC CAG GTG AGA AAG ATC GAG ATT GTG               256
Leu Arg Pro Val Gln Val Arg Lys Ile Glu Ile Val
         70                  75

CGG AAG AAG CCA ATC TTT AAG AAG GCC ACG GTG ACG               292
Arg Lys Lys Pro Ile Phe Lys Lys Ala Thr Val Thr
 80              85                          90

CTG GAG GAC CAC CTG GCA TGC AAG TGT GAG ACA GTG               328
Leu Glu Asp His Leu Ala Cys Lys Cys Glu Thr Val
             95              100

GCA GCT GCA CGG CCT GTG ACC CGA AGC CCG GGG GTT               364
Ala Ala Ala Arg Pro Val Thr Arg Ser Pro Gly Gly
    105                      110             115

GGT TCC CAG GAG CAG CGA TAAG                                  386
Ser Gln Glu Gln Arg
                120
```